US012685786B2

(12) United States Patent
Cho et al.

(10) Patent No.: US 12,685,786 B2
(45) Date of Patent: Jul. 21, 2026

(54) TREATMENT OF NERVE DAMAGE USING 5'UTR OF Gpr151 GENE OR VARIANT THEREOF

(71) Applicant: Daegu Gyeongbuk Institute of Science & Technology, Daegu (KR)

(72) Inventors: Yongcheol Cho, Seoul (KR); Jung Eun Shin, Seoul (KR); Jinyoung Lee, Daejeon (KR); Bohm Lee, Seocho-gu (KR); Yewon Jeon, Seoul (KR)

(73) Assignee: DAEGU GYEONGBUK INSTITUTE OF SCIENCE & TECHNOLOGY(DGIST), Daegu (KR)

( * ) Notice: Subject to any disclaimer, the term of this patent is extended or adjusted under 35 U.S.C. 154(b) by 412 days.

(21) Appl. No.: 18/278,037

(22) PCT Filed: Feb. 18, 2022

(86) PCT No.: PCT/KR2022/002459
§ 371 (c)(1),
(2) Date: Aug. 21, 2023

(87) PCT Pub. No.: WO2022/177369
PCT Pub. Date: Aug. 25, 2022

(65) Prior Publication Data
US 2024/0382618 A1     Nov. 21, 2024

(30) Foreign Application Priority Data
Feb. 19, 2021    (KR) ........................ 10-2021-0022790

(51) Int. Cl.
*A61K 48/00*        (2006.01)
*A61K 38/00*        (2006.01)
*A61P 25/28*        (2006.01)
*C07K 14/47*        (2006.01)
*C12N 15/86*        (2006.01)

(52) U.S. Cl.
CPC ............ *A61K 48/005* (2013.01); *A61P 25/28* (2018.01); *C07K 14/4722* (2013.01); *C12N 15/86* (2013.01); *A61K 38/00* (2013.01); *C12N 2740/15043* (2013.01)

(58) Field of Classification Search
CPC .. A61K 48/005; A61K 38/00; A61K 31/7088; A61K 48/00; A61P 25/28; C07K 14/4722; C07K 14/47; C12N 15/86; C12N 2740/15043; C12N 2750/14143
See application file for complete search history.

(56) References Cited

U.S. PATENT DOCUMENTS

2004/0123338 A1* 6/2004 Fincher ................ C07K 14/415
800/278
2007/0231263 A1    10/2007 Qiu et al.

FOREIGN PATENT DOCUMENTS

WO      WO-0168843 A1 *  9/2001  ............. C07K 14/72
WO      2009-141066      11/2009

OTHER PUBLICATIONS

"NM_194251" (National Library of Medicine Accession No. 194251; published Dec. 12, 2019) (Year: 2019).*
Jiang ("Demethylation of G-protein-coupled receptor 151 promoter facilitates the binding of Krüppel-like factor 5 and enhances neuropathic pain after nerve injury in mice." Journal of Neuroscience 38.49 (2018): 10535-10551) (Year: 2018).*
NCBI, GenBank Accession No. NM_194251.3, 'Homo sapiens G protein-coupled receptor 151 (GPR151), mRNA', Dec. 15, 2020.
Jonas Broms et al., "Monosynaptic retrograde tracing of neurons expressing the G-protein coupled receptor Gpr151 in the mouse brain", Journal of Comparative Neurology, 2017, 525, p. 3227-3250 3228, 3247-3248.
Bohm Lee et al., "Promoting axon regeneration by enhancing the non-coding function of the injury-responsive coding gene Gpr151", Aug. 14, 2021, p. 1-6, https://www.biorxiv.org/content/10.1101/2021.02.19.431965v2.full.pdf.
Bao-Chun Jiang et al., "G protein-coupled receptor GPR151 is involved in trigeminal neuropathic pain through the induction of Gβγ/extracellular signal-regulated kinase-mediated neuroinflammation in the trigeminal ganglion," Pain, vol. 162, No. 5, pp. 1434-1448, Nov. 2020, doi: https://doi.org/10.1097/j.pain.0000000000002156.
Josette J Wlaschin et al., "Dual leucine zipper kinase is required for mechanical allodynia and microgliosis after nerve injury," eLife, vol. 7, Jul. 2018, doi: https://doi.org/10.7554/elife.33910.
Beatriz Antolin-Fontes et al., "The habenular G-protein-coupled receptor 151 regulates synaptic plasticity and nicotine intake," Proceedings of the National Academy of Sciences of the United States of America, vol. 117, No. 10, pp. 5502-5509, Feb. 2020, doi: https://doi.org/10.1073/pnas.1916132117.
Manuel Gey et al., "Atf3 mutant mice show reduced axon regeneration and impaired regeneration-associated gene induction after peripheral nerve injury," Open Biology, vol. 6, No. 8, p. 160091, Aug. 2016, doi: https://doi.org/10.1098/rsob.160091.
Florence Allain et al., "The mu opioid receptor and the orphan receptor GPR151 contribute to social reward in the habenula," Scientific Reports, vol. 12, No. 1, Nov. 2022, doi: https://doi.org/10.1038/s41598-022-24395-z.

(Continued)

*Primary Examiner* — Neil P Hammell
*Assistant Examiner* — Kyle T Rega
(74) *Attorney, Agent, or Firm* — LEX IP MEISTER, PLLC

(57)                    ABSTRACT

Disclosed is a composition for treating a neurological disease caused by nerve injury, including an isolated polynucleotide of a 5'-untranslated region (5'UTR) of a Gpr151 gene or a variant thereof. Also disclosed are a novel variant polynucleotide of 5'UTR of a Gpr151 gene and a vector including the polynucleotide.

11 Claims, 31 Drawing Sheets

Specification includes a Sequence Listing.

(56)          References Cited

OTHER PUBLICATIONS

Fiona E. Holmes et al., "Targeted disruption of the orphan receptor
Gpr151 does not alter pain-related behaviour despite a strong
induction in dorsal root ganglion expression in a model of neuropathic
pain," Molecular and Cellular Neuroscience, vol. 78, pp. 35-40, Jan.
2017, doi: https://doi.org/10.1016/j.mon.2016.11.010.

* cited by examiner

[Fig. 1a]
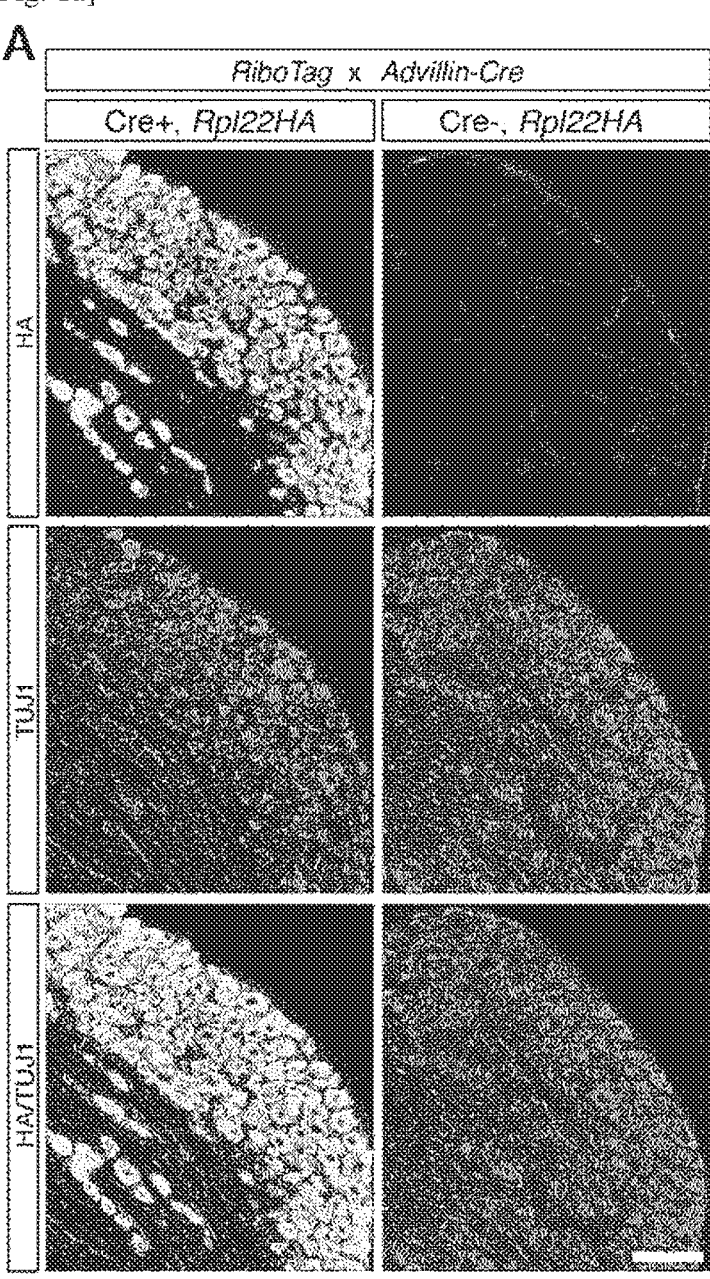

[Fig. 1b]
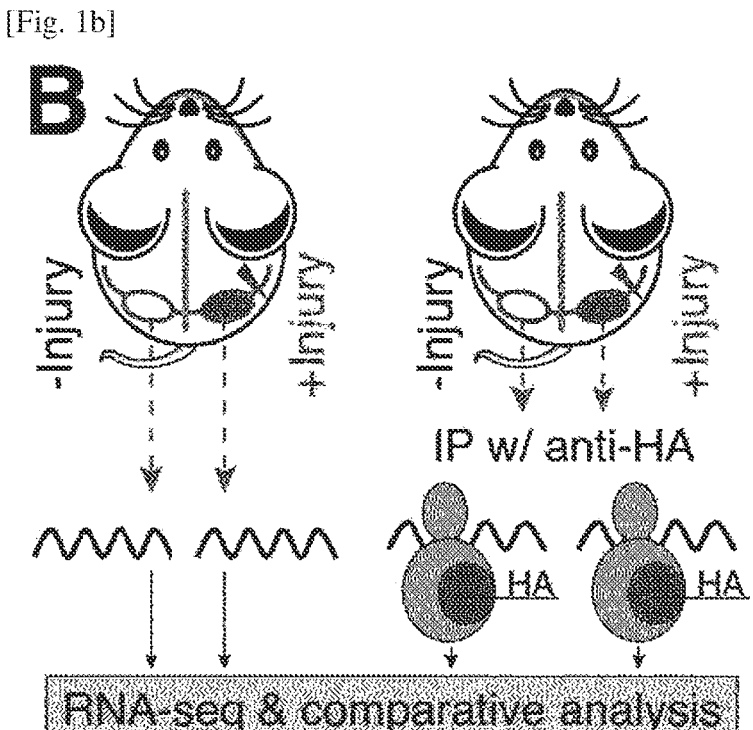

| | | |
|---|---|---|
| Areg 7.4 | Csf1 2.9 | Stk32a 1.9 |
| Cckbr 6.8 | Arc 2.9 | Rhoq 1.9 |
| Saa1 6.2 | Gal 2.8 | Itga7 1.9 |
| Ece1 6.1 | Nts 2.8 | Ifrd1 1.8 |
| Atf3 5.9 | Arid5a 2.7 | Nkain1 1.7 |
| Rasef 5.7 | Vgf 2.7 | Sbno2 1.7 |
| Sdr42e1 5.3 | Tmem88b 2.6 | Tes 1.7 |
| Adm2 5.2 | Arhgef15 2.5 | Galnt9 1.7 |
| Slc6a4 5.2 | Fam124a 2.5 | Serpinb1a 1.7 |
| Krt6a 5.2 | Plekha7 2.4 | St6galnac4 1.7 |
| Olfr920 5.2 | Fosl2 2.4 | Gm20481 1.6 |
| Sprr1a 5.1 | Tmem74b 2.3 | Trex1 1.6 |
| Serpine1 4.7 | Stmn4 2.3 | Rnf122 1.6 |
| Smim3 4.7 | Igfbp3 2.3 | Arhgap22 1.6 |
| Flrt3 4.7 | Adam8 2.3 | Cebpd 1.6 |
| Plaur 4.2 | Fam111a 2.3 | Irs2 1.6 |
| Gpr151 4.0 | Mchr1 2.2 | Sez6l 1.6 |
| Fgf3 3.9 | Nfil3 2.2 | Pfkfb4 1.6 |
| Gadd45a 3.7 | Chac1 2.2 | 9030624G23Rik 1.6 |
| Timp1 3.6 | Gadd45g 2.1 | C1qb 1.6 |
| Npy 3.6 | Npy1r 2.1 | Mt2 1.6 |
| Sema6a 3.5 | Zfp772 2.1 | Tubb6 1.5 |
| Gm10406 3.4 | Tnfrsf12a 2.0 | Sdc1 1.5 |
| Csrnp1 3.3 | Xdh 2.0 | Hr 1.5 |
| Msh6 3.3 | Igsf9b 2.0 | Fam53c 1.5 |
| Sox11 3.2 | Kif22 2.0 | Gpr19 1.5 |
| Procr 3.2 | Slc29a2 1.9 | Tle3 1.5 |
| Tecta 3.2 | Camk1 1.9 | Fads3 1.5 |
| Adcyap1 3.1 | Jun 1.9 | Fam210b 1.5 |
| Fst 3.1 | F13a1 1.9 | |
| Pmaip1 3.0 | Ogdhl 1.9 | |

8.8

Log2[Average reads @24hr]

1.8

[Fig. 1e]
[Fig. 1f]
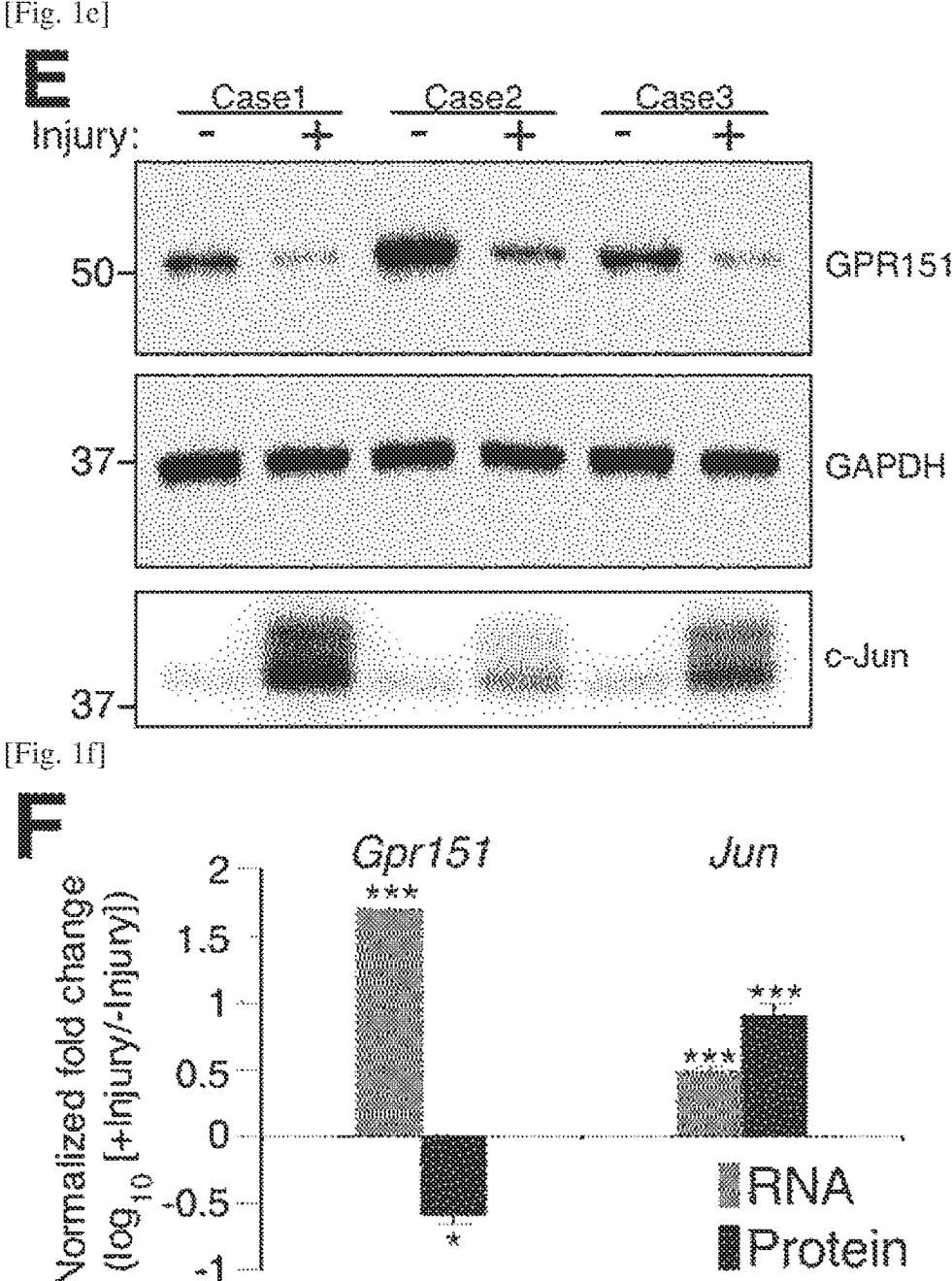

[Fig. 1g]
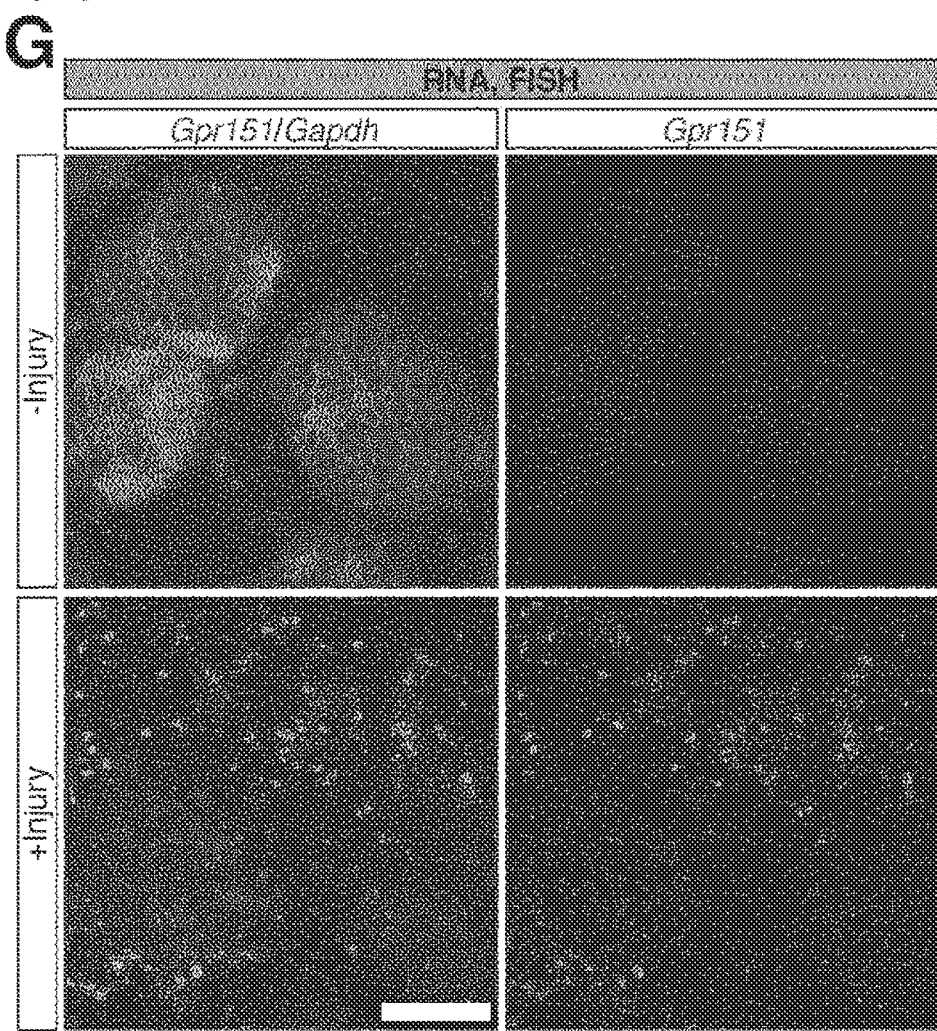

[Fig. 1h]
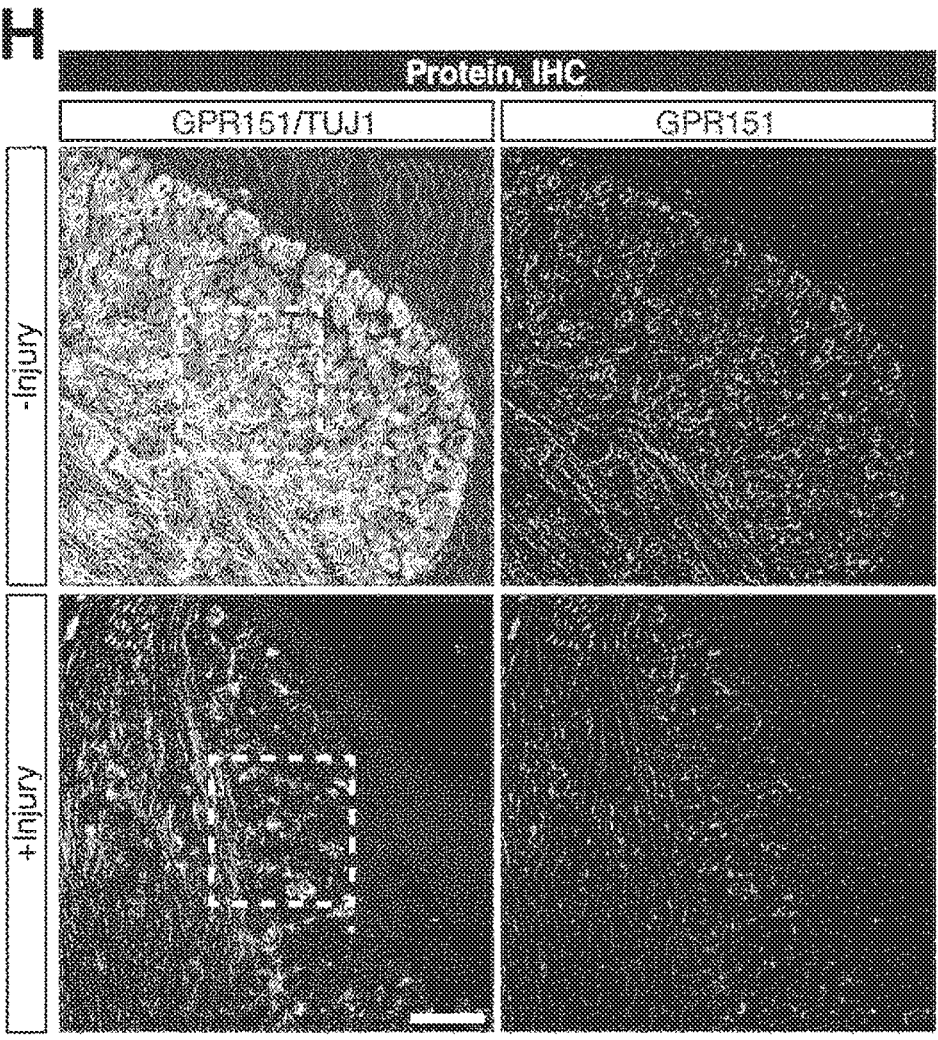

[Fig. 2a]
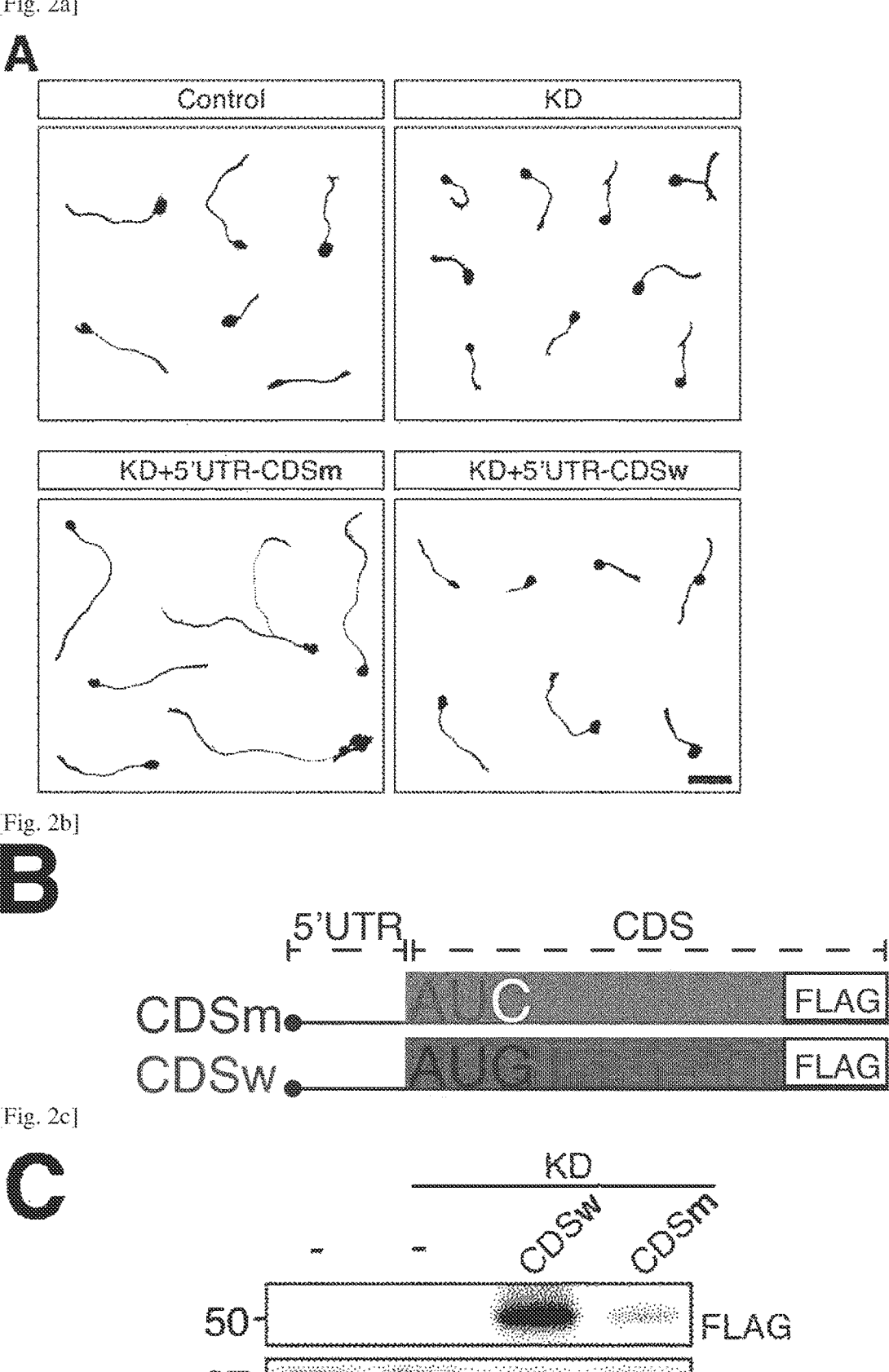
[Fig. 2b]
[Fig. 2c]

[Fig. 2d]
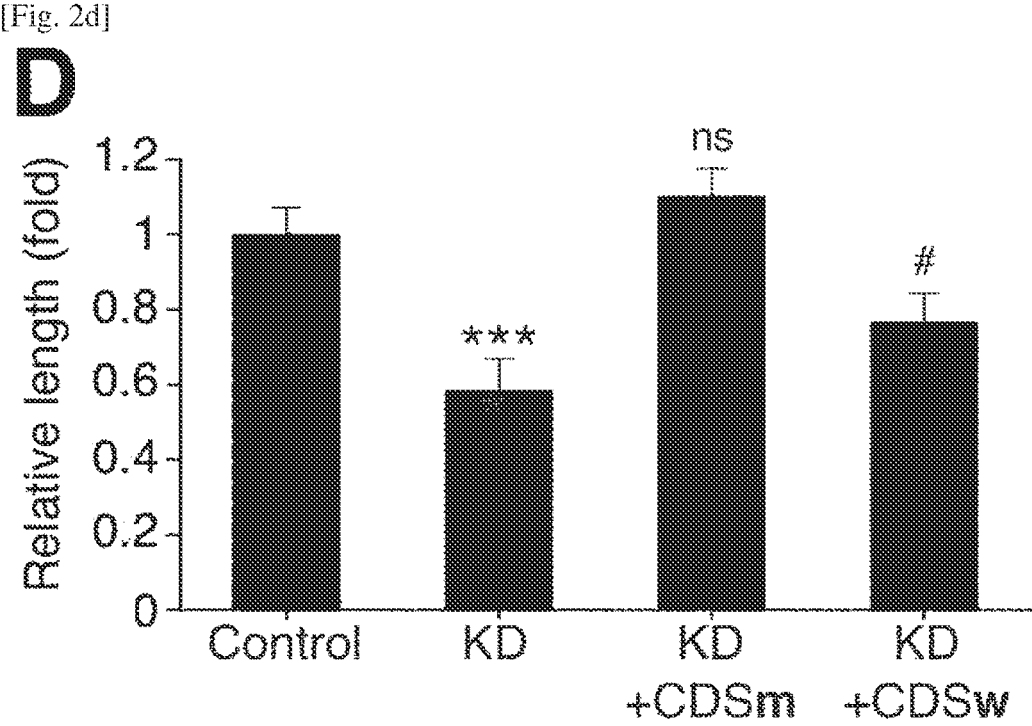
[Fig. 2e]
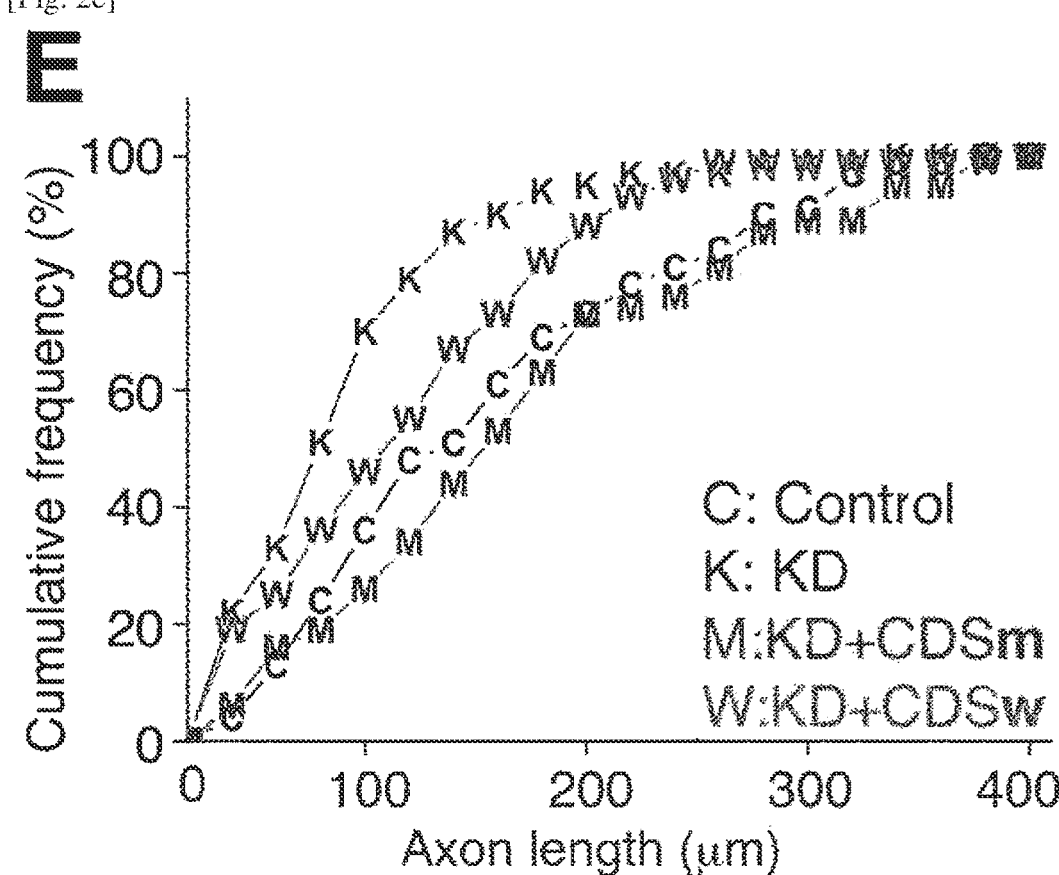

[Fig. 2f]
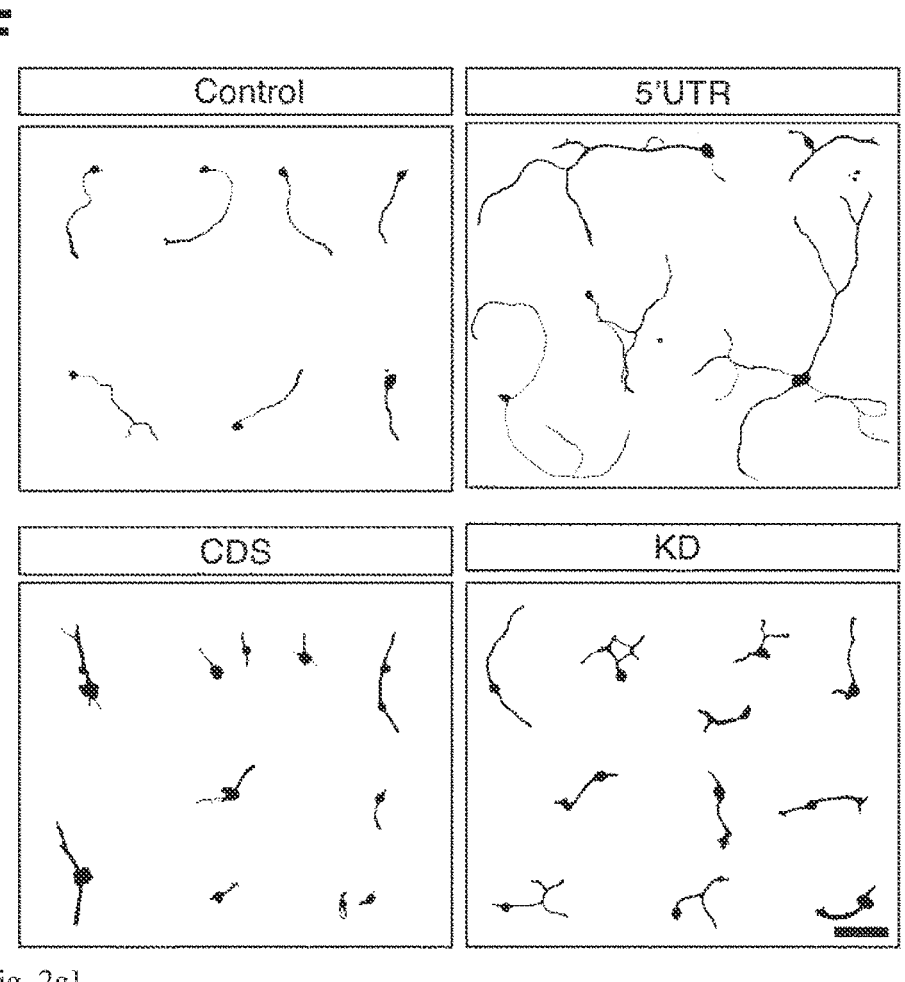
[Fig. 2g]
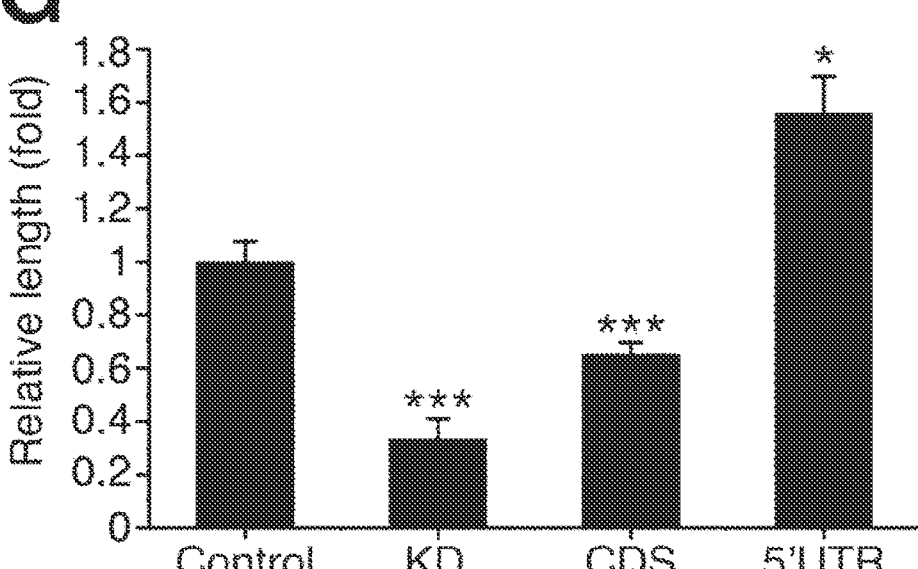

[Fig. 3a]
A
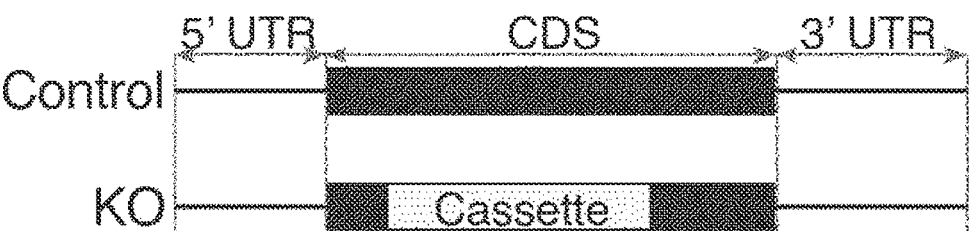
[Fig. 3b]
B
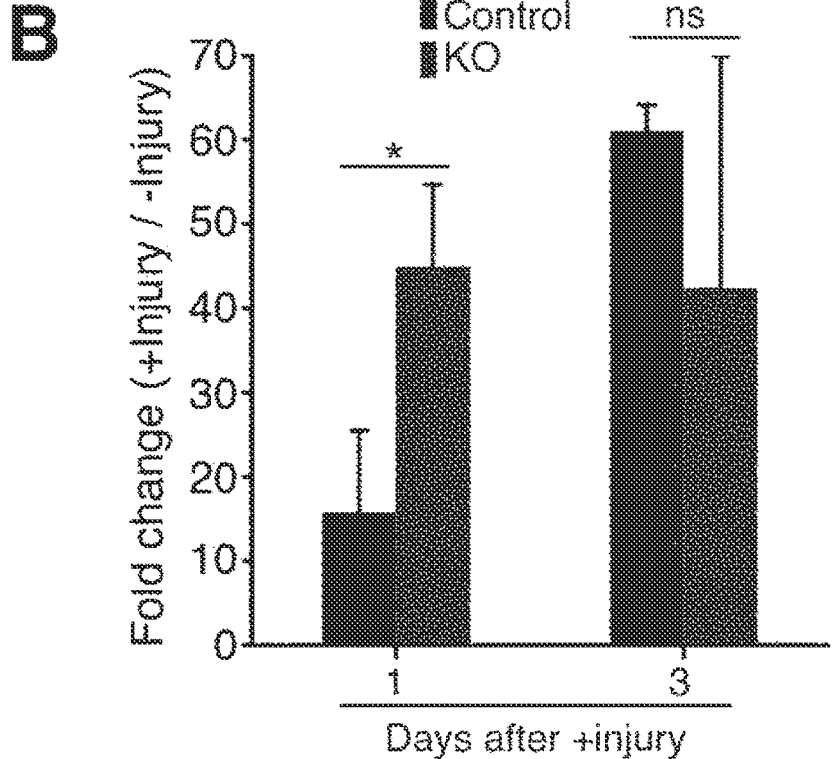

[Fig. 3c]
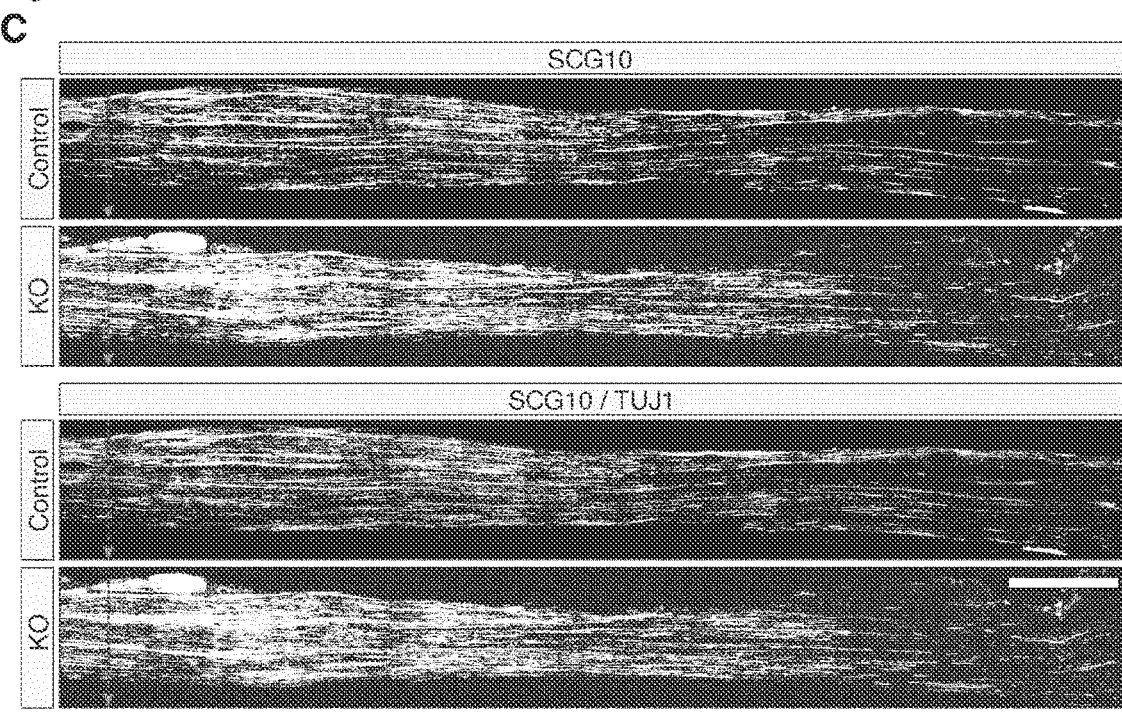
[Fig. 3d]
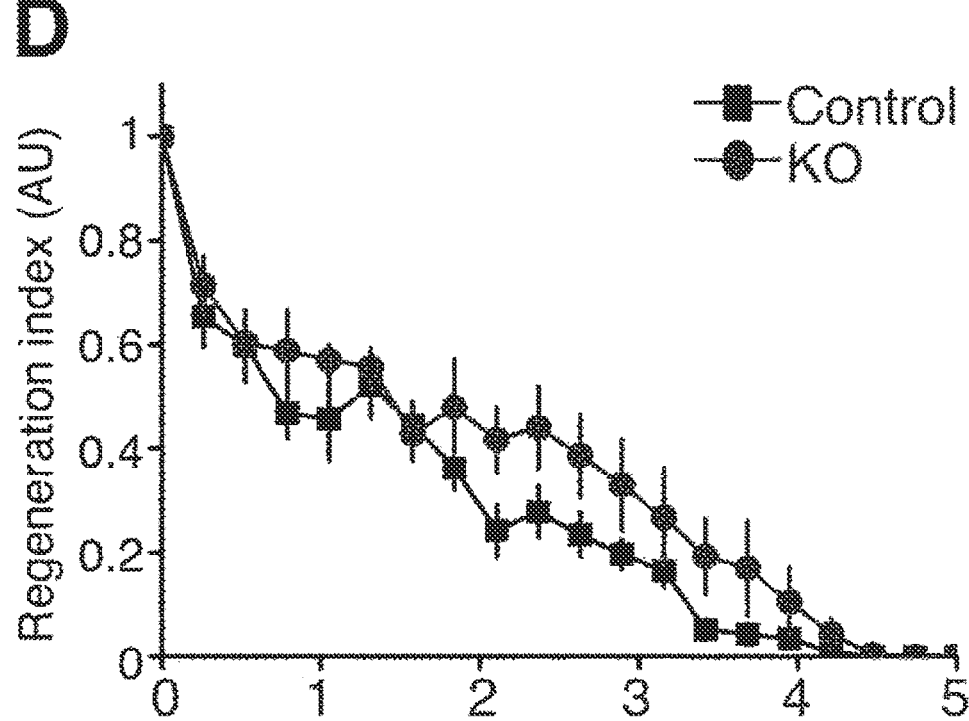

[Fig. 3e]
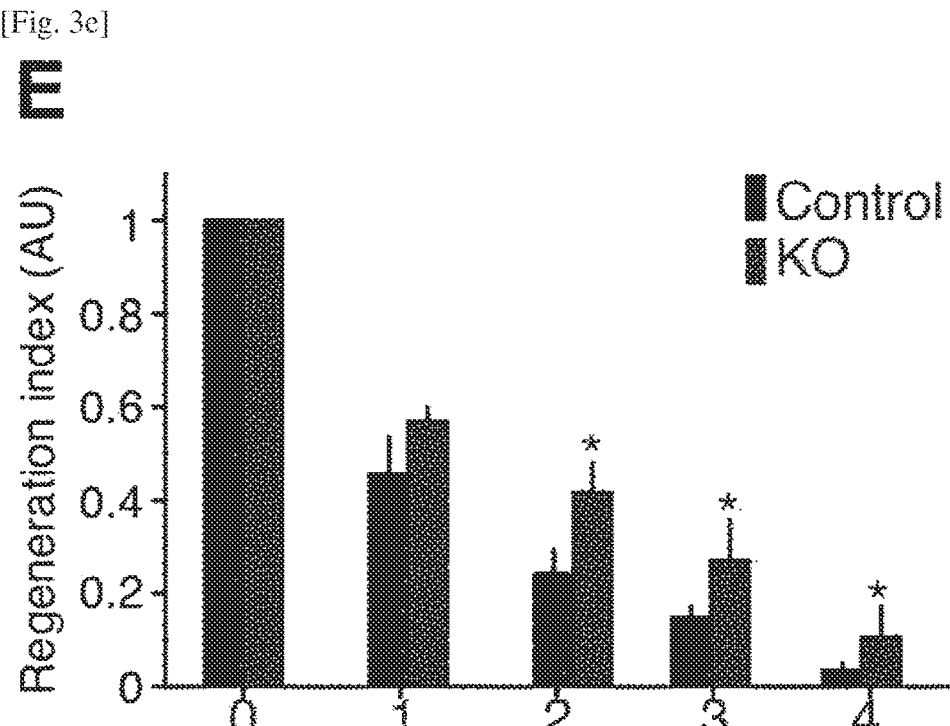
[Fig. 3f]
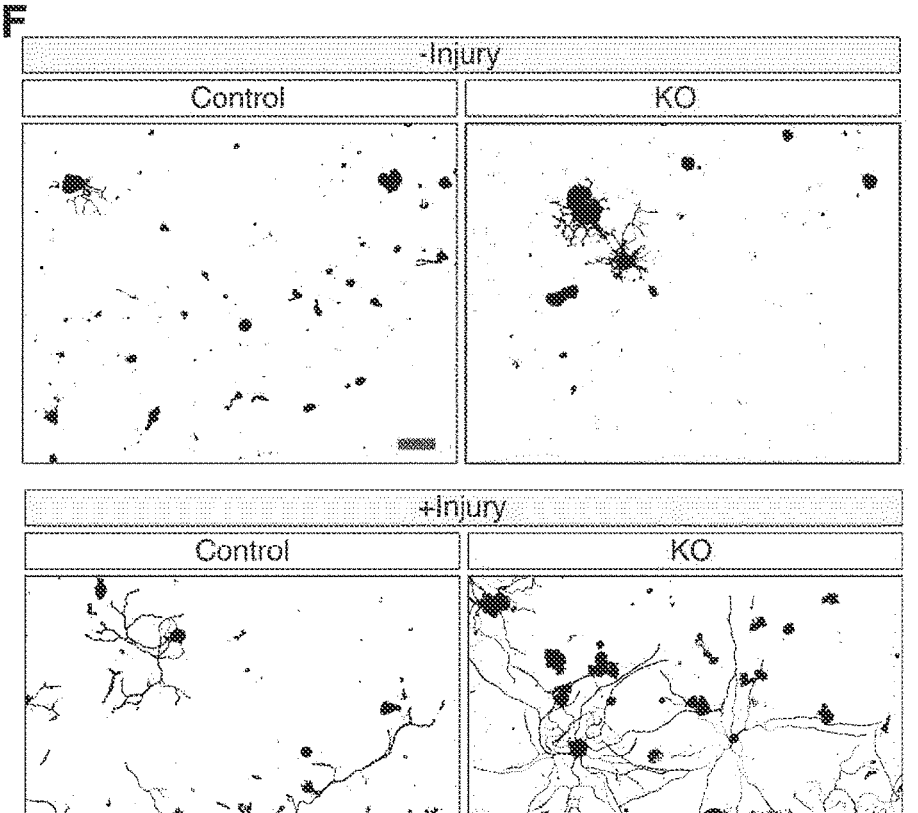

[Fig. 3g]
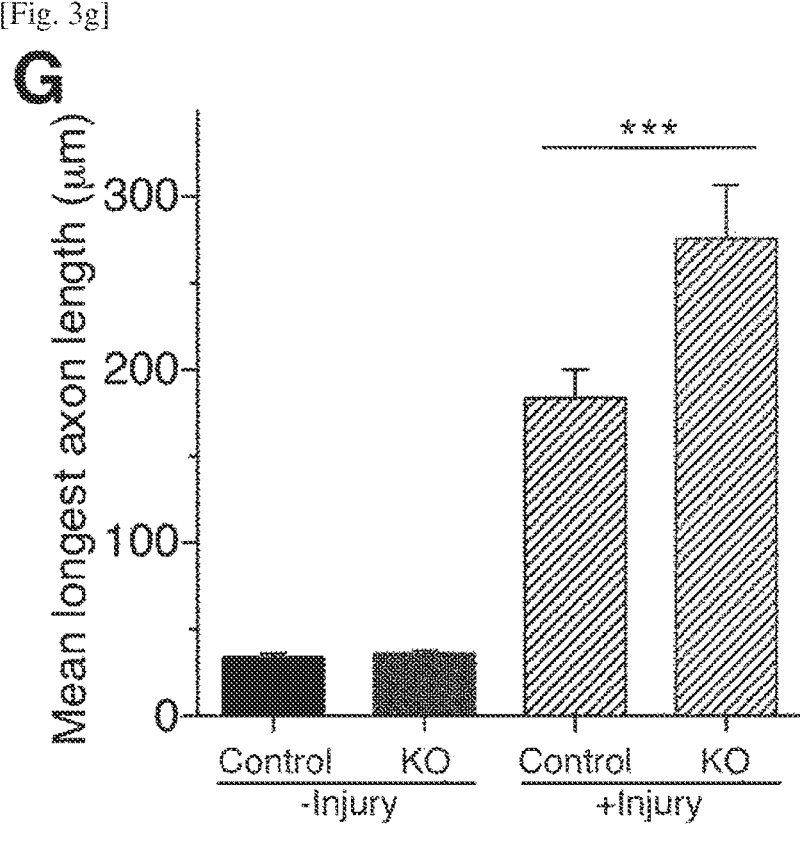
[Fig. 3h]
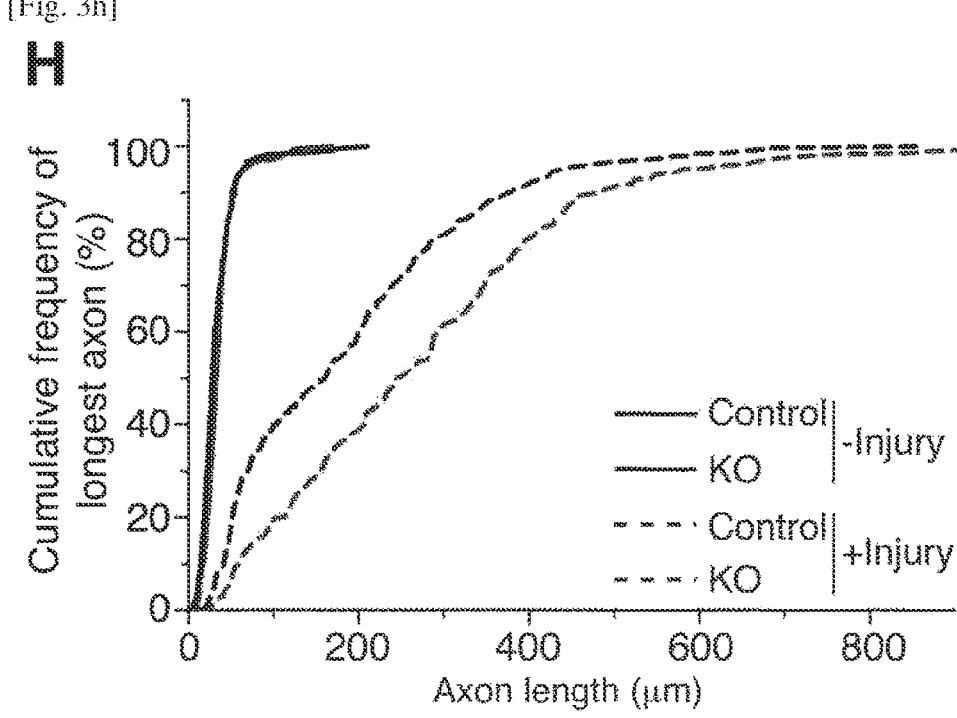

[Fig. 3i]
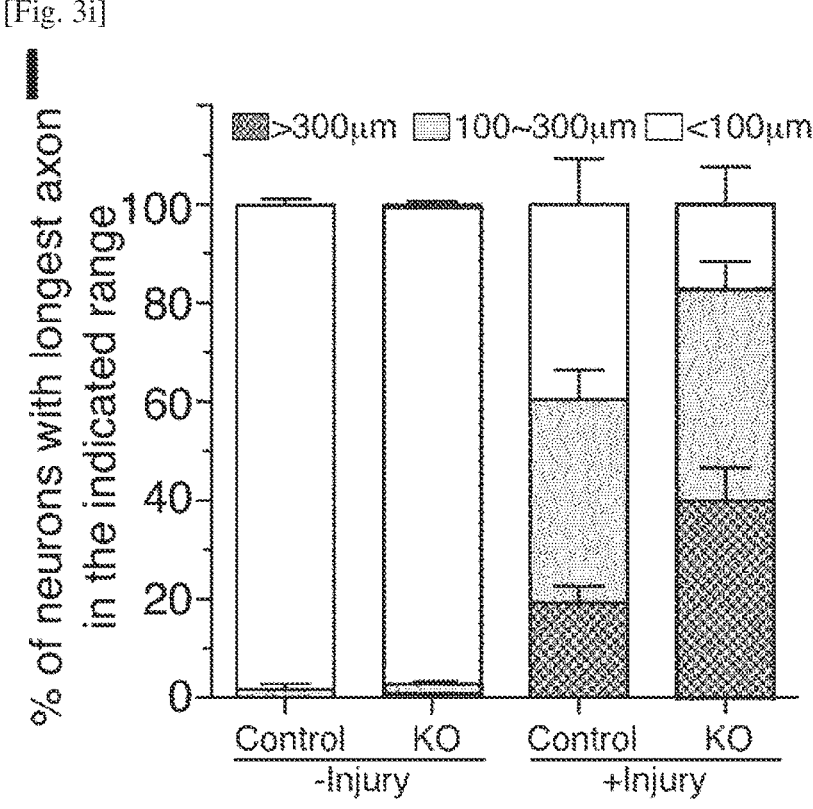

[Fig. 4a]
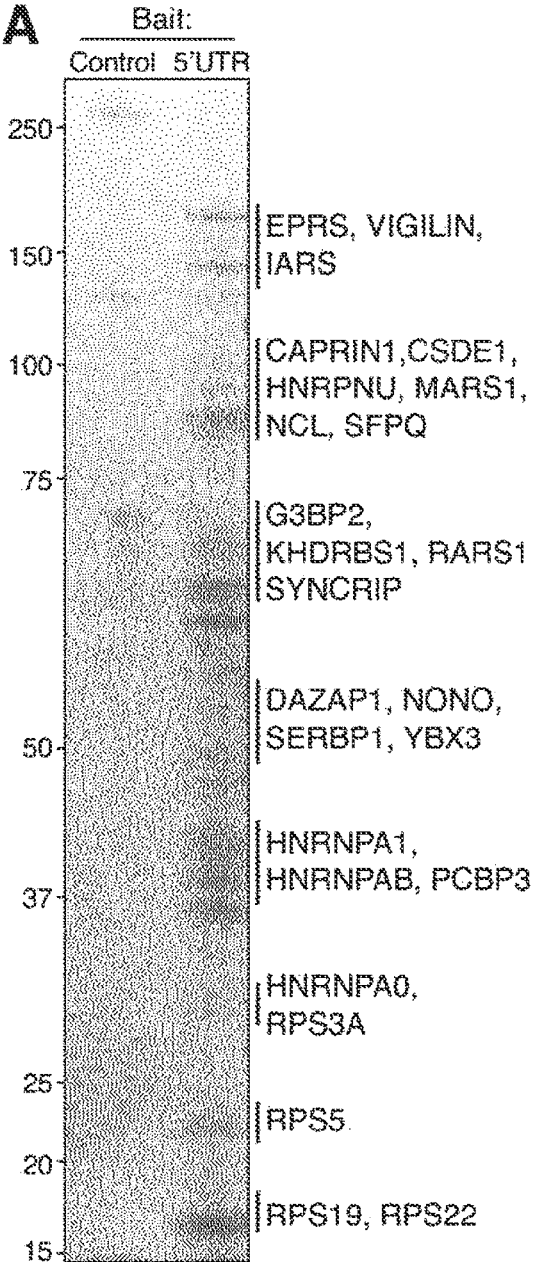
A
EPRS, VIGILIN,
IARS
CAPRIN1,CSDE1,
HNRPNU, MARS1,
NCL, SFPQ
G3BP2,
KHDRBS1, RARS1
SYNCRIP
DAZAP1, NONO,
SERBP1, YBX3
HNRNPA1,
HNRNPAB, PCBP3
HNRNPA0,
RPS3A
RPS5
RPS19, RPS22
[Fig. 4b]
B
```
Mouse  CCAACCTAAACAAGAAGCTACCATCTGCAGGGAGG-----AGCTTGATG
Rat    ACCAACCTAATAAGAAGCTAACATCTGCAGGGAGG-----AGCTGGATG
Human  CAAACCTAAATAAGAATCTAACTTCTGTAAGAAGCTGTGAAGAGTGATG
             *     **_******* ***    **** * *  **     **    ****
```

[Fig. 4c]
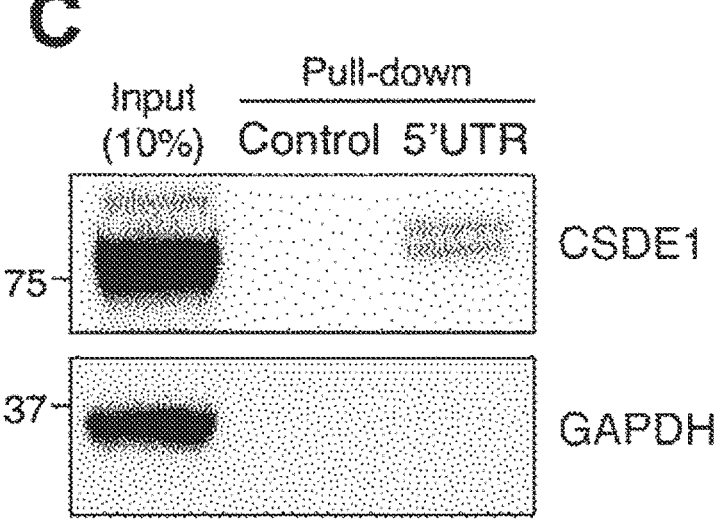
[Fig. 4d]
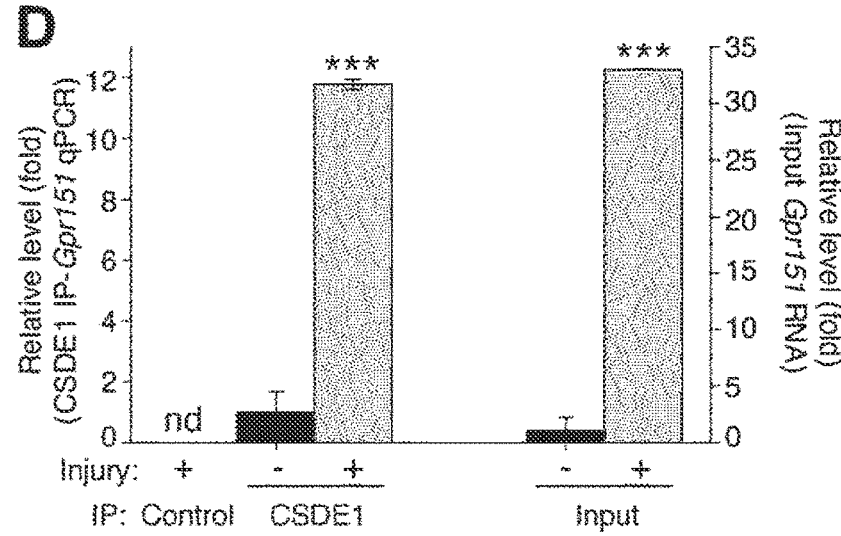
[Fig. 4e]
E
5'UTRWT ————————————— CAAGAA —————————
ΔCSDE1 ———————————————————————————————
4X ACAAGAAGACAAGAAGACAAGAAGACAAGAAG
[Fig. 4f]
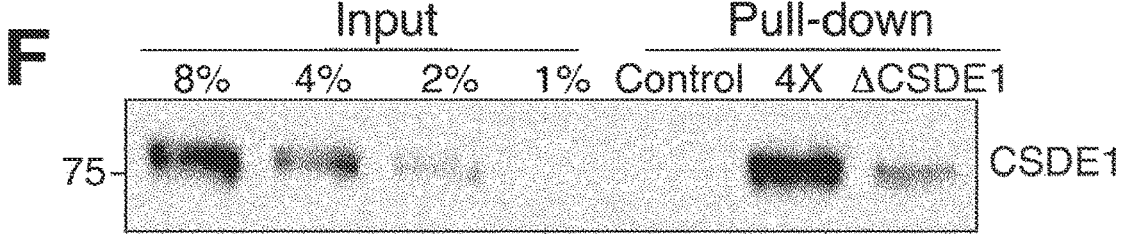

[Fig. 4i]
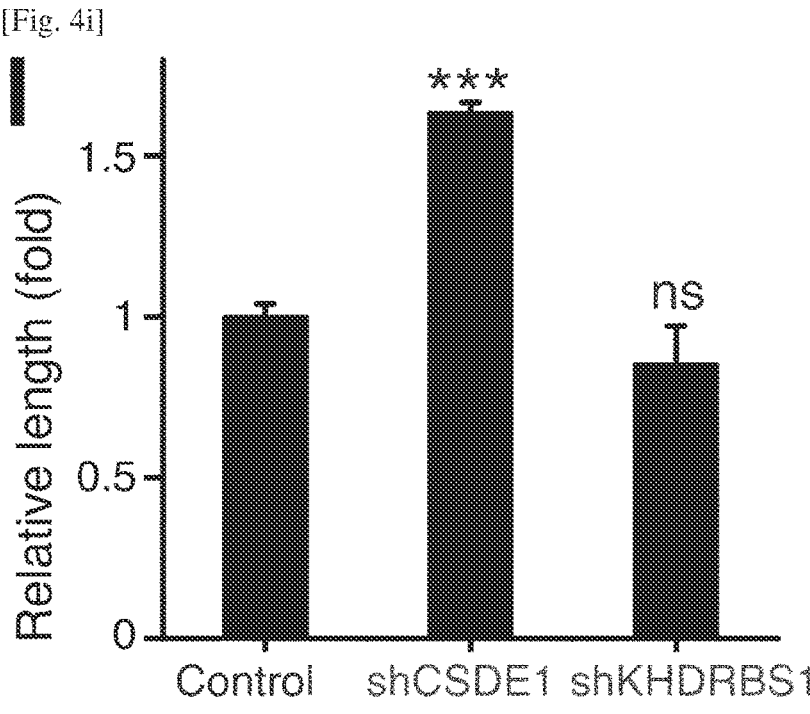
[Fig. 4j]
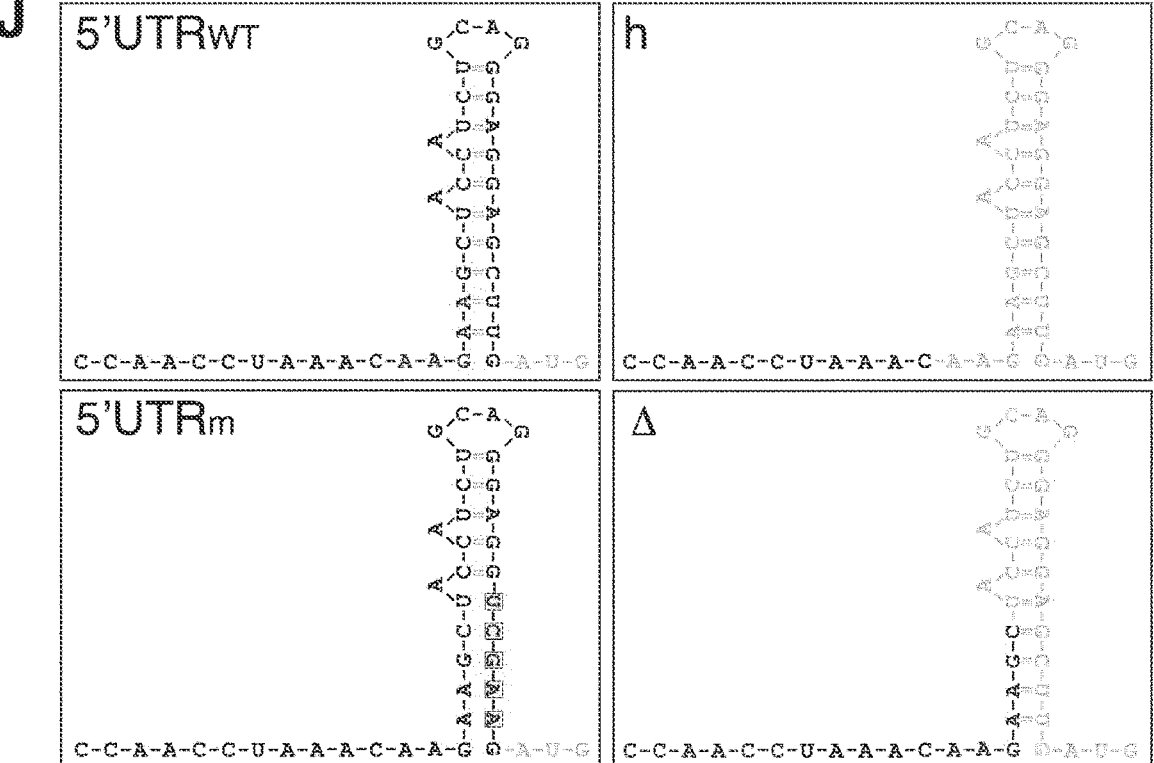

[Fig. 4k]
[Fig. 4l]
[Fig. 4m]
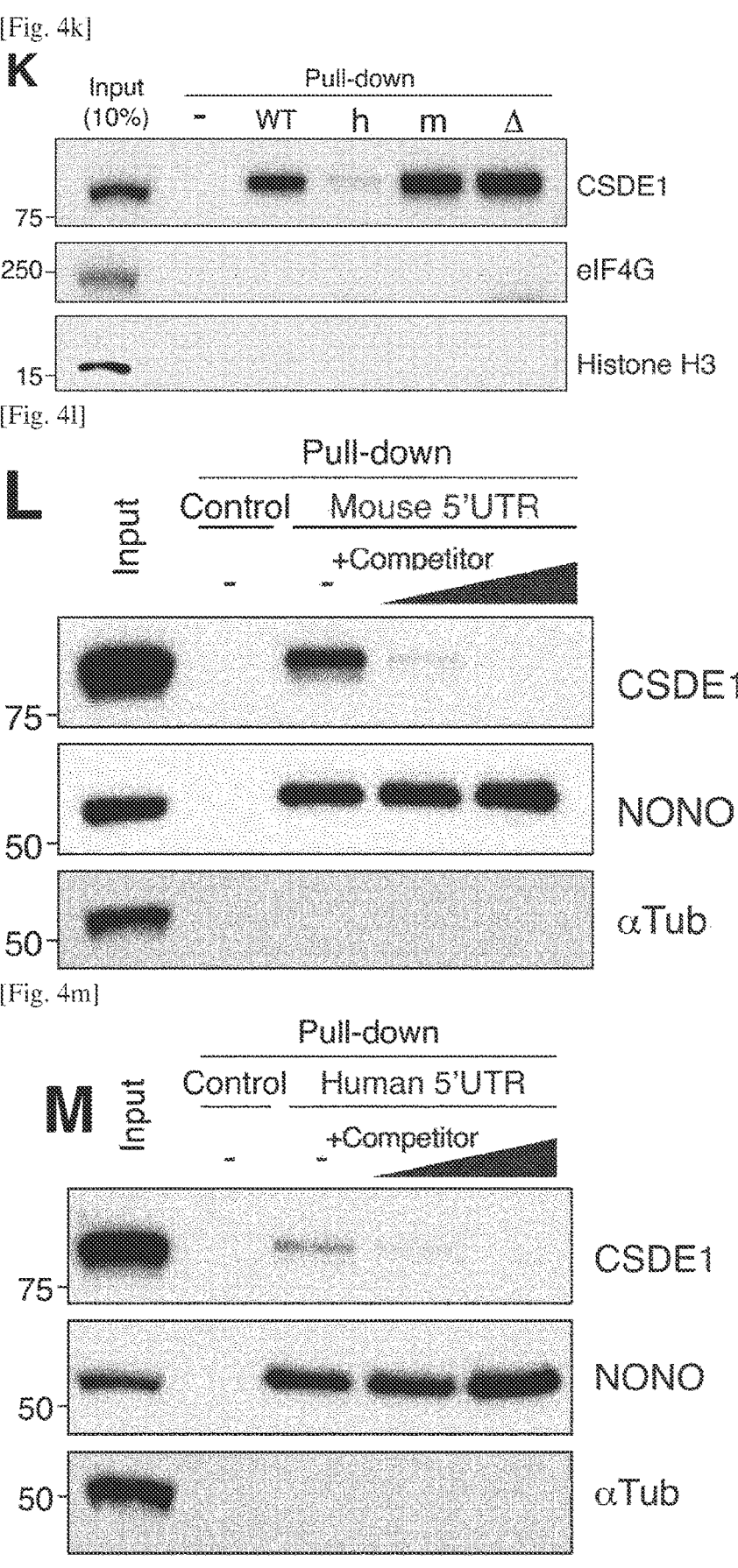

[Fig. 5a]
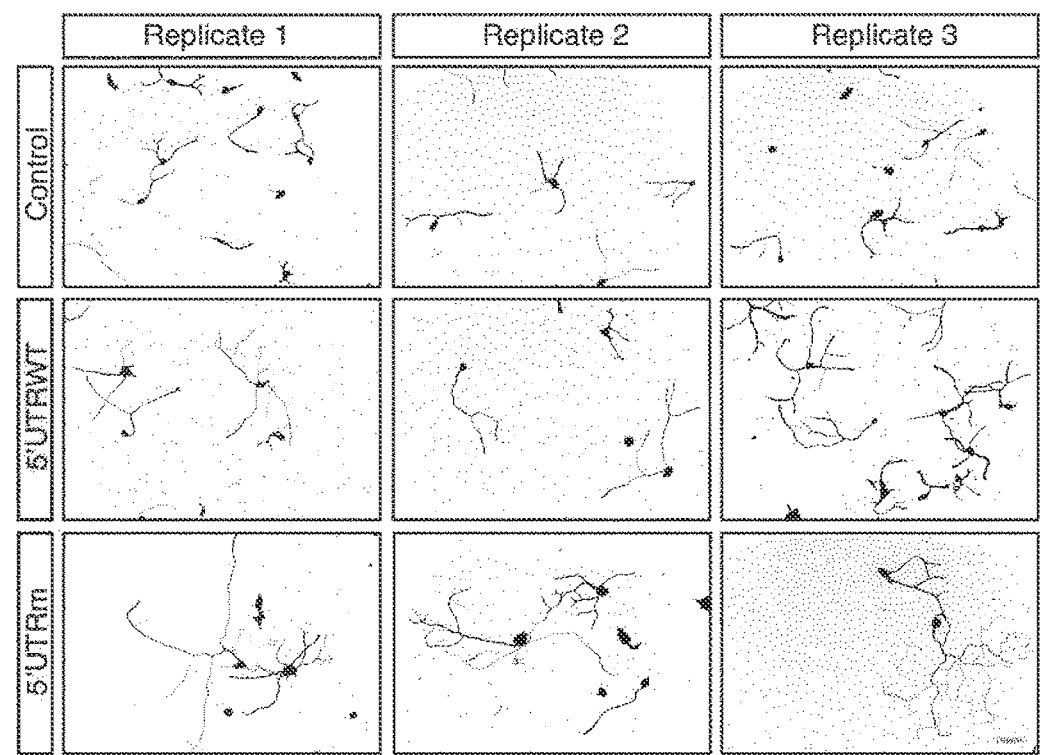
[Fig. 5b]
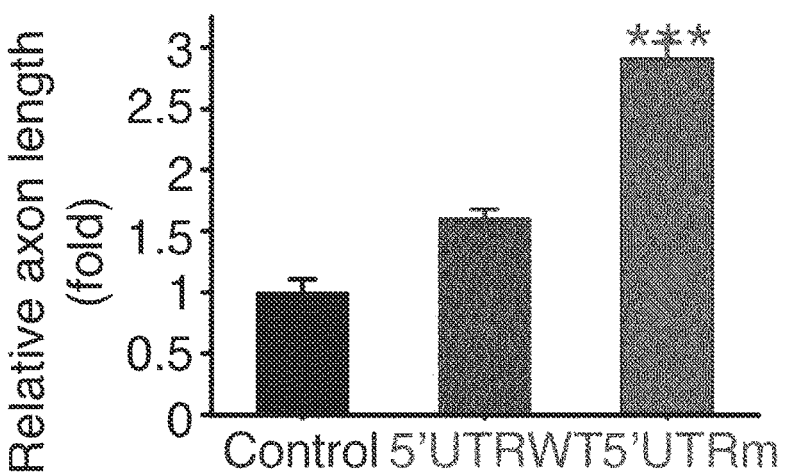

[Fig. 5c]
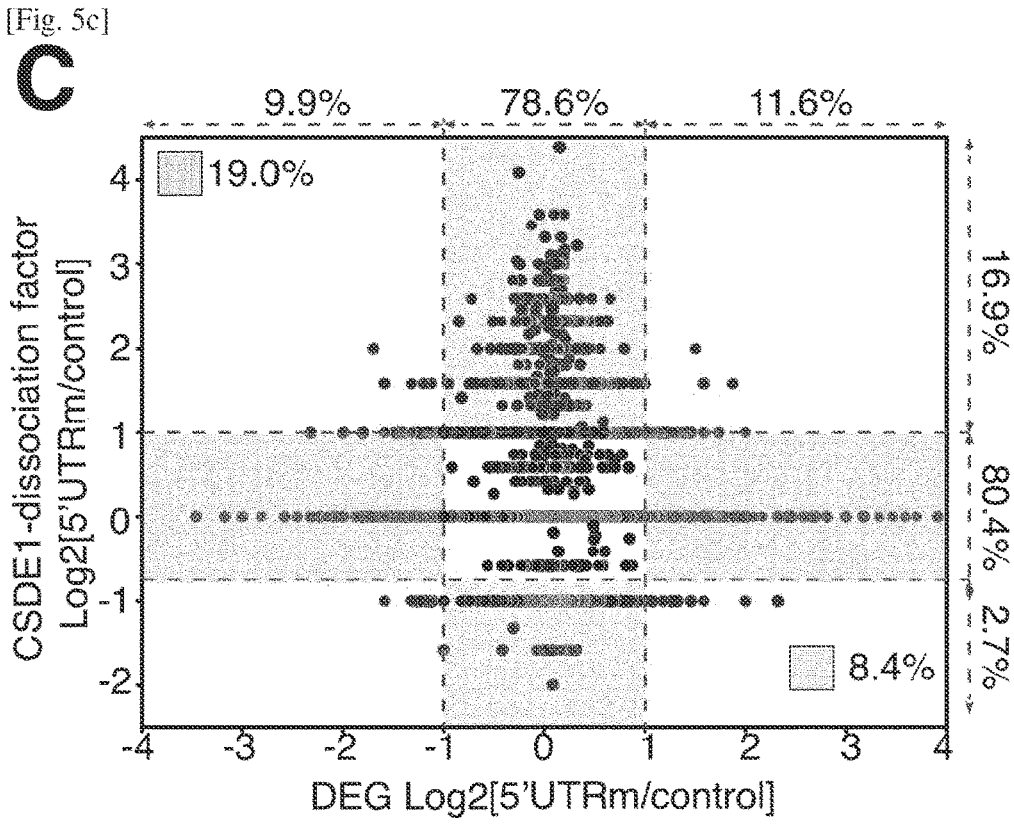
[Fig. 5d]
D

[Fig. 5e]
E
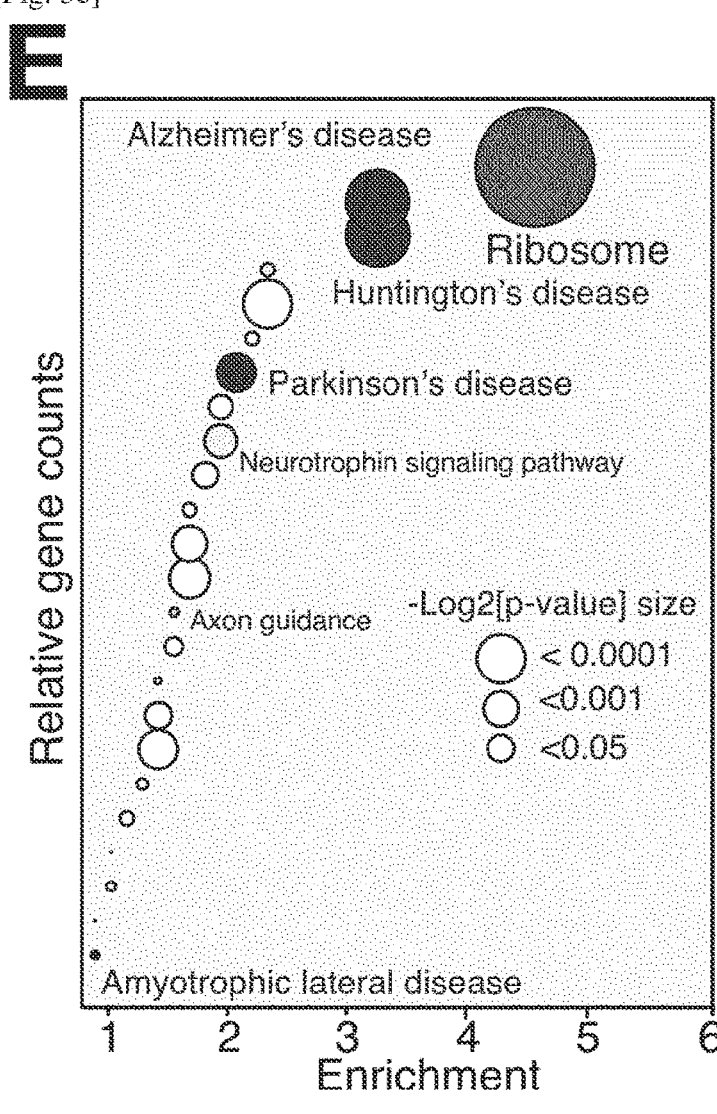

[Fig. 5f]
F
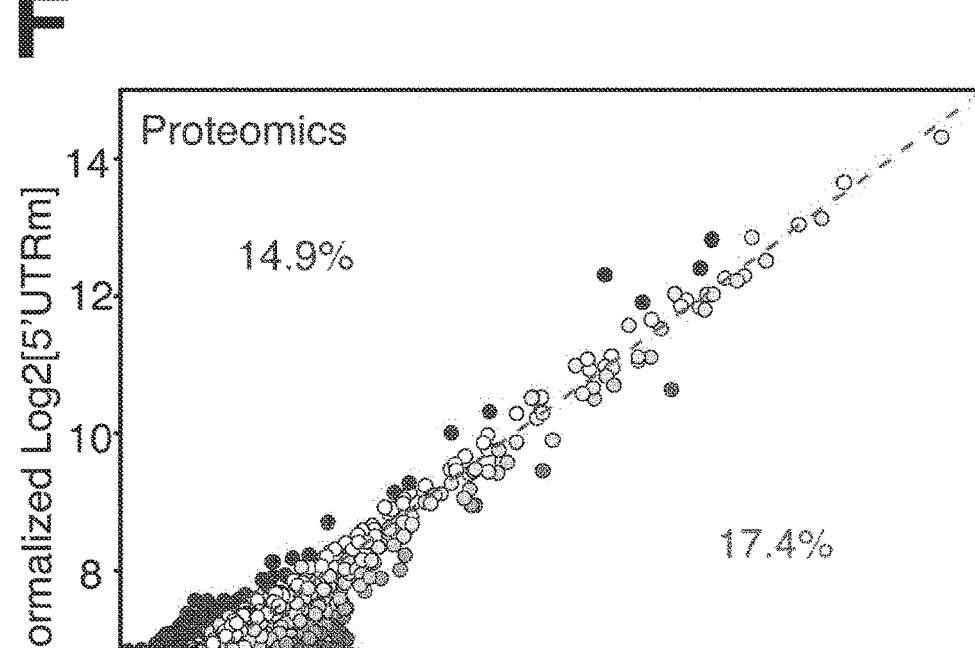
[Fig. 5g]
G
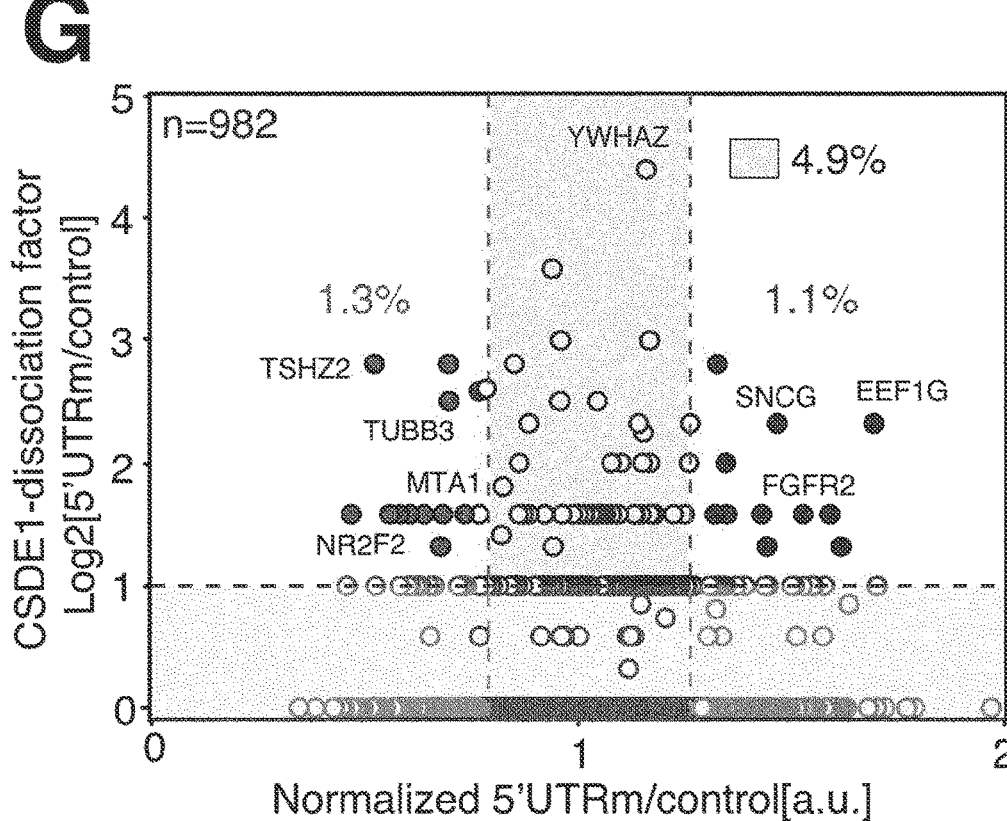

[Fig. 6a]

In vivo gene delivery     +12wk +Injury     +3days Assay

[Fig. 6b]

[Fig. 6c]
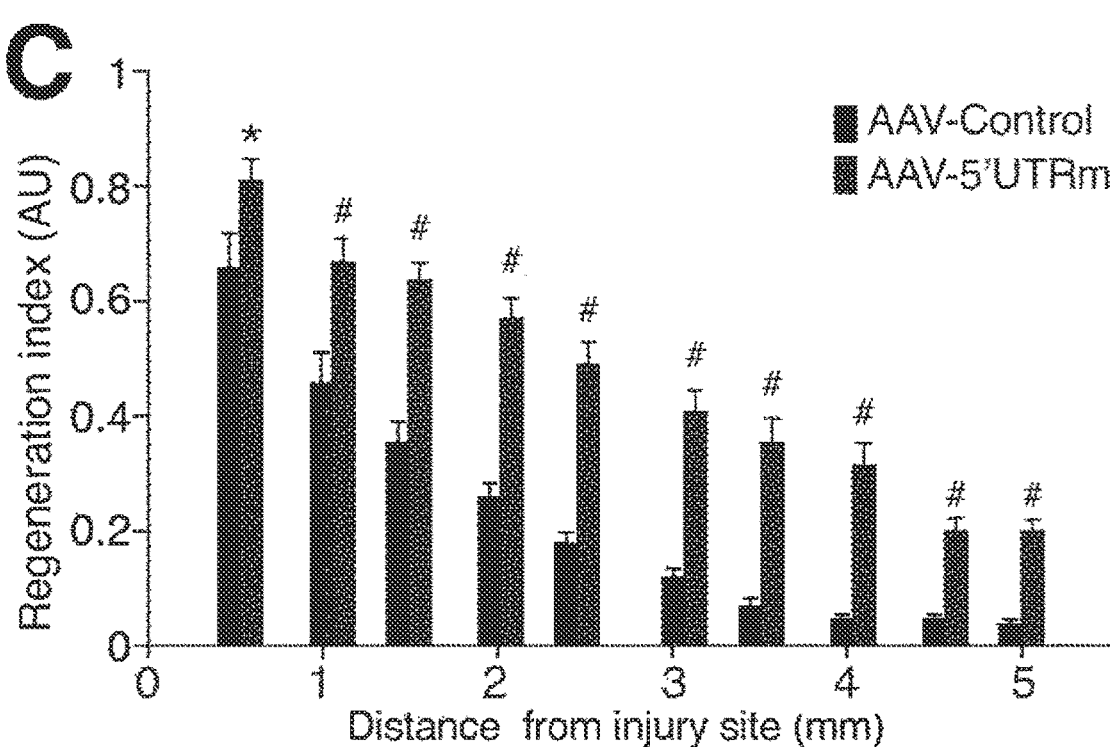
[Fig. 6d]
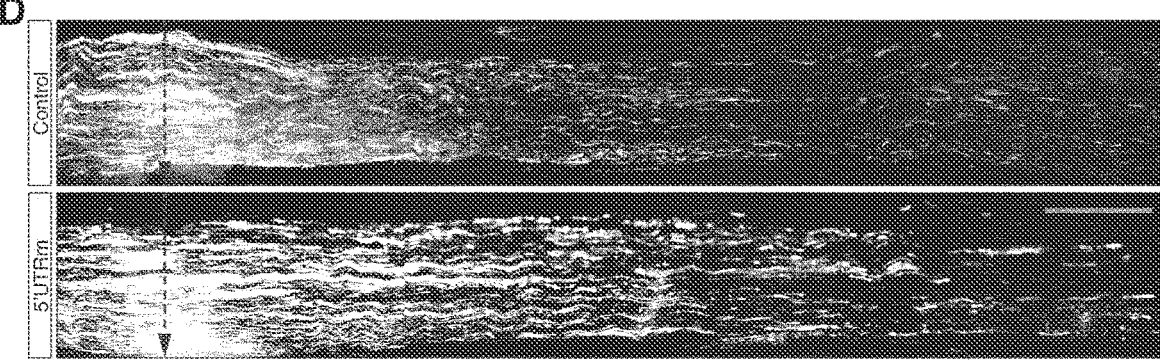
[Fig. 6e]
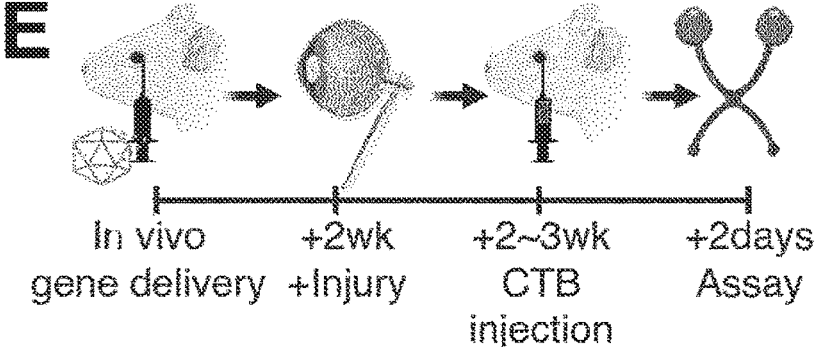

[Fig. 6f]
F
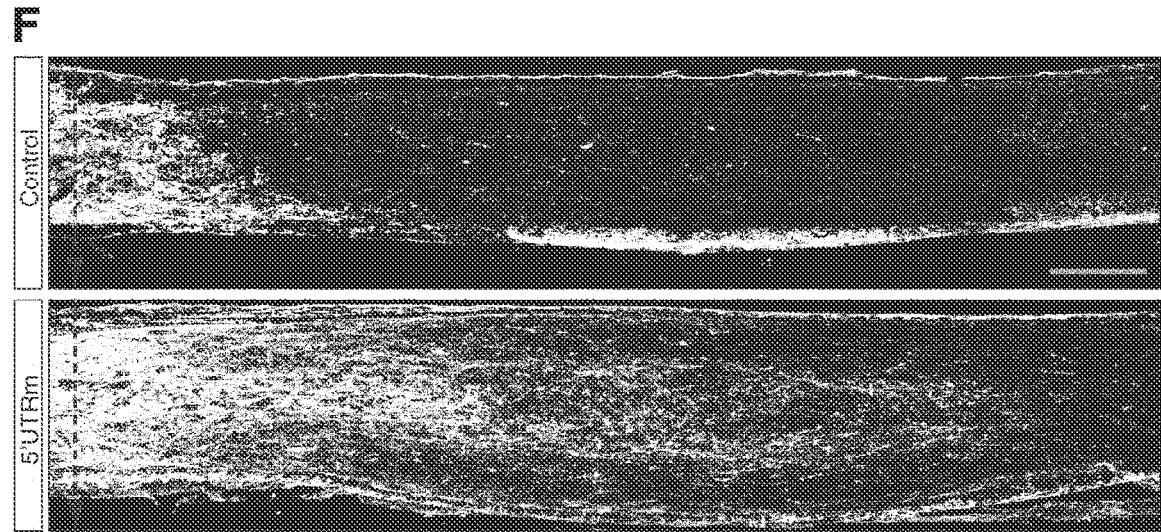
[Fig. 6g]
G
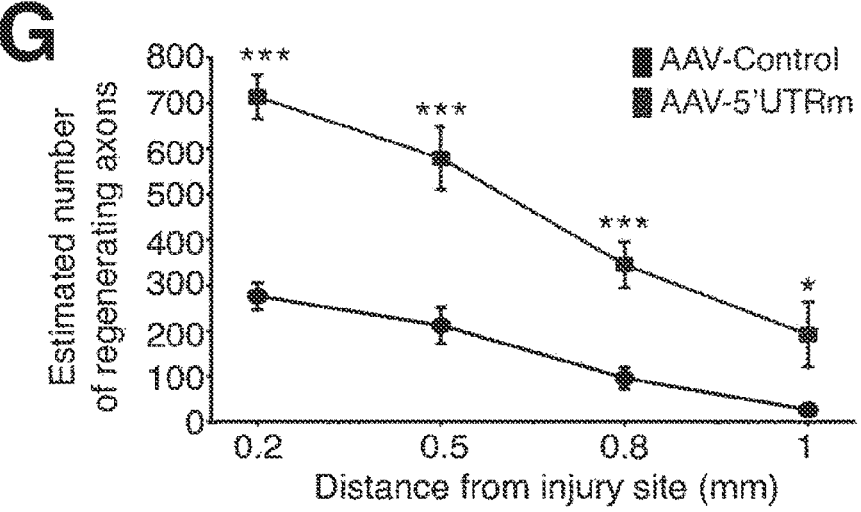

[Fig. 6h]
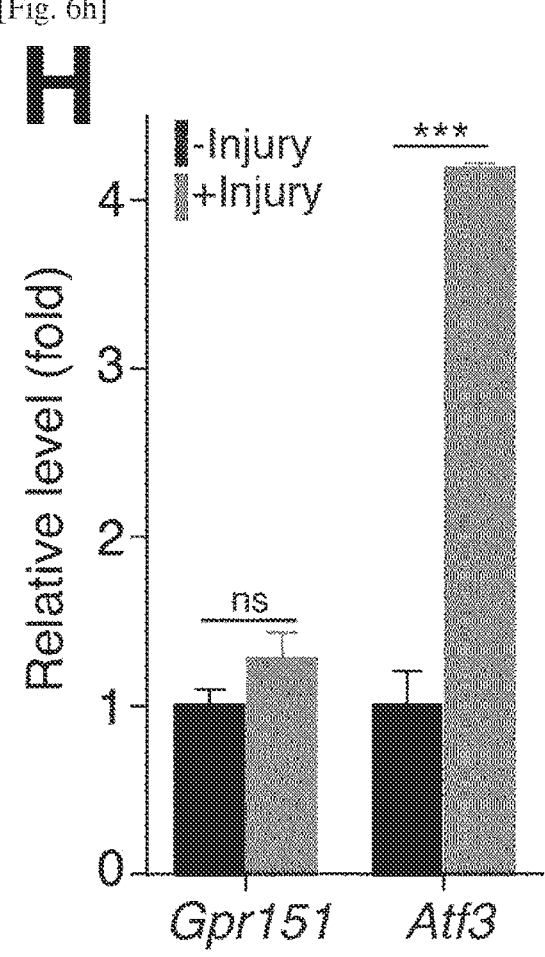

[Fig. 7a]
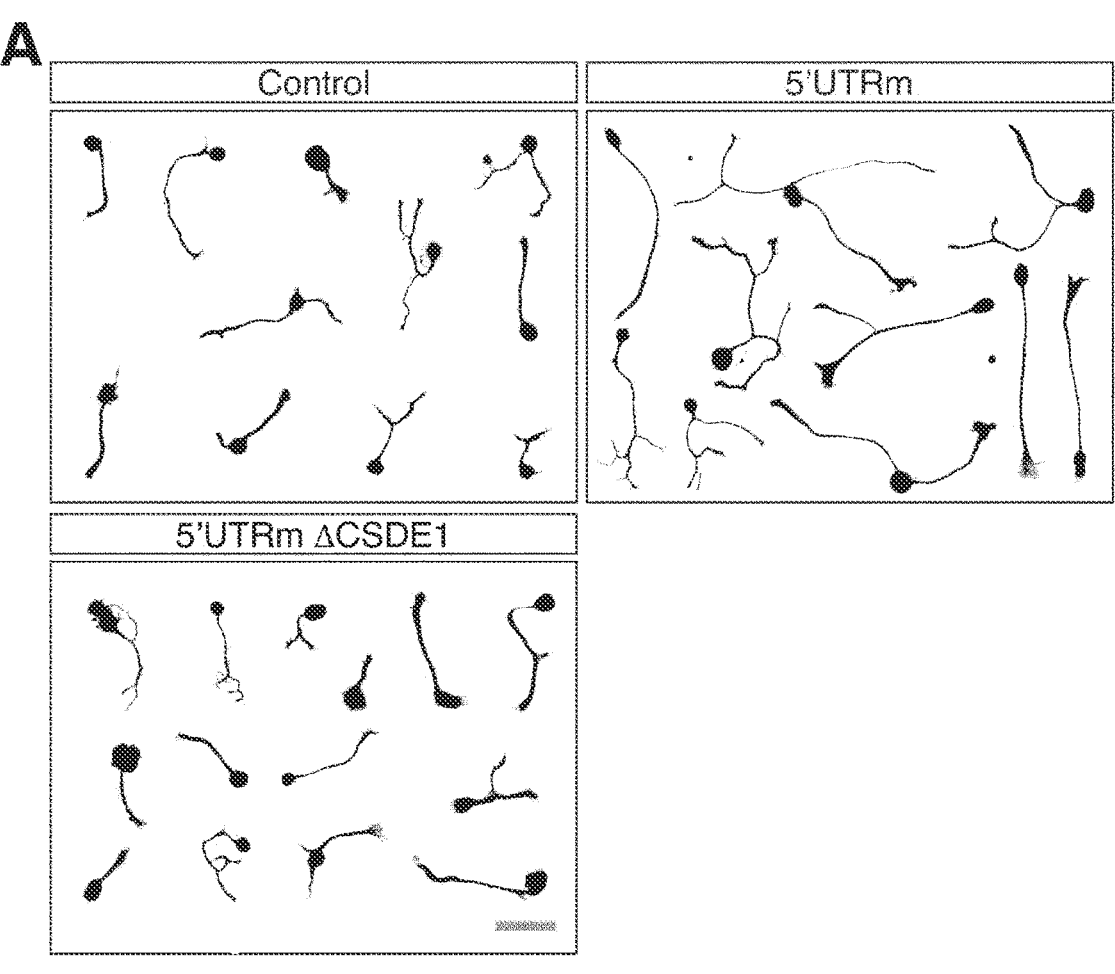
[Fig. 7b]
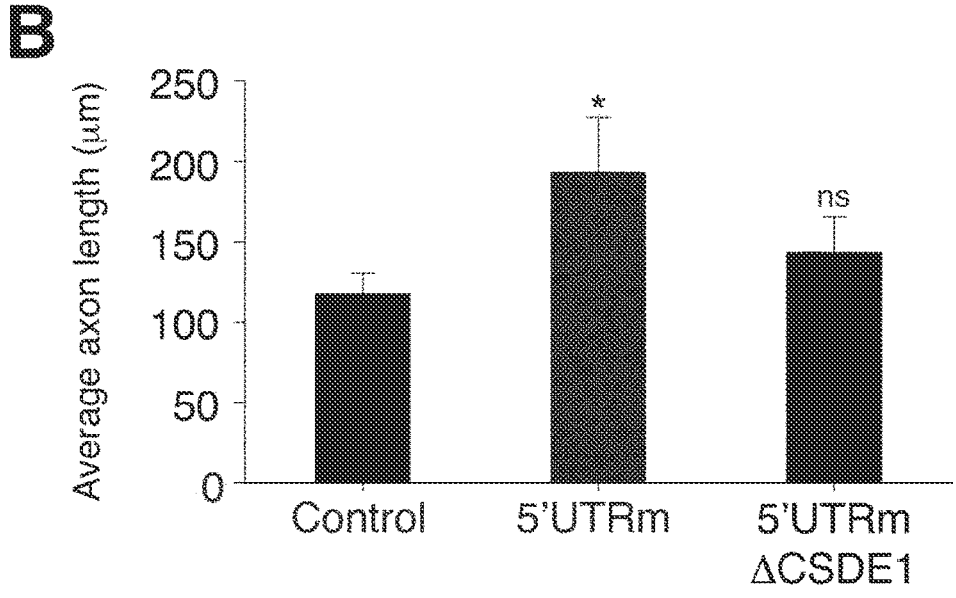

[Fig. 8]
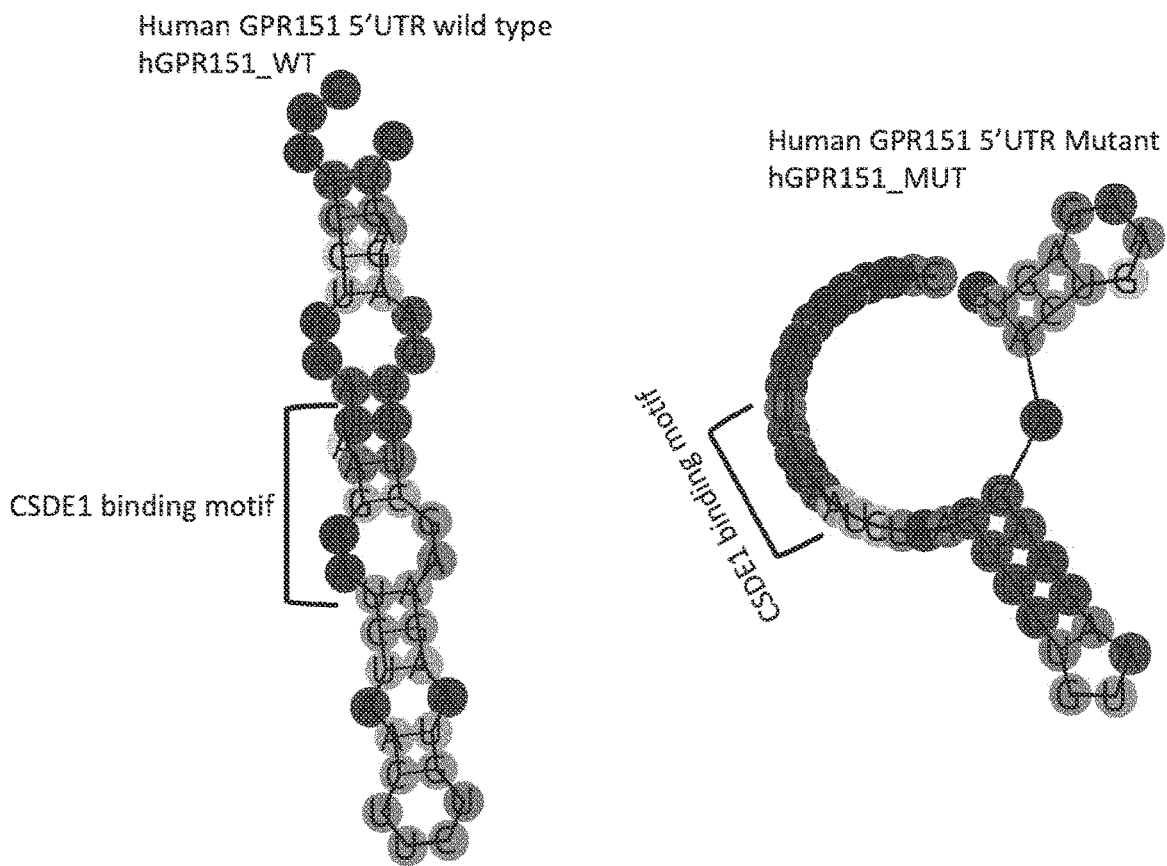
[Fig. 9a]
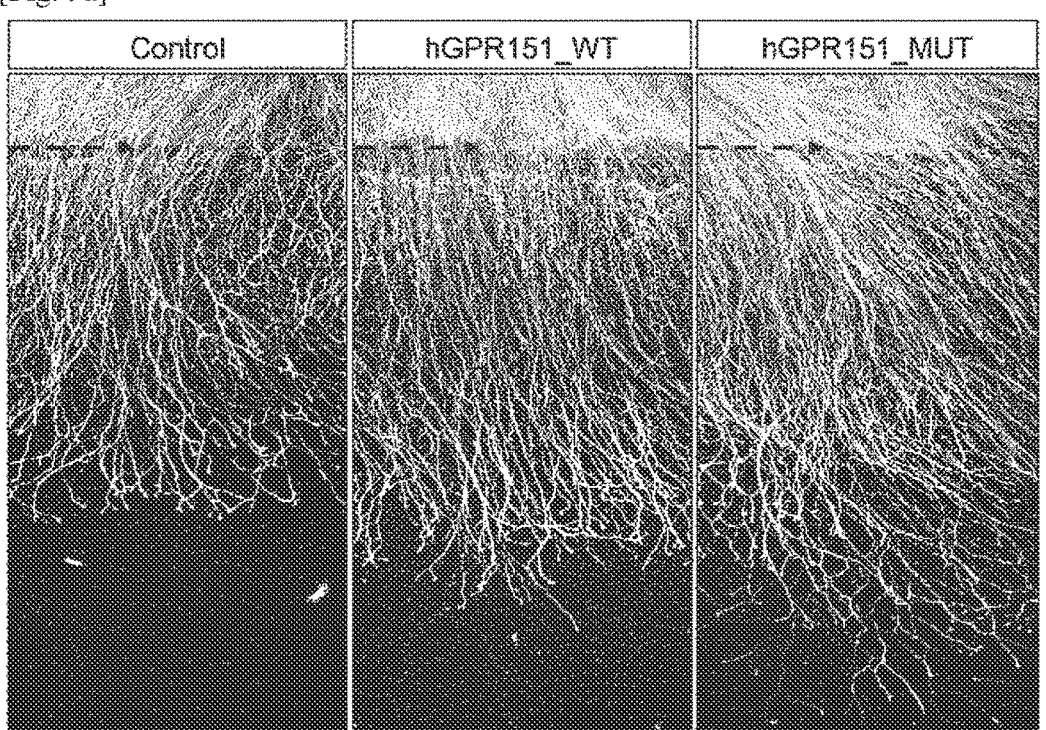

[Fig. 9b]
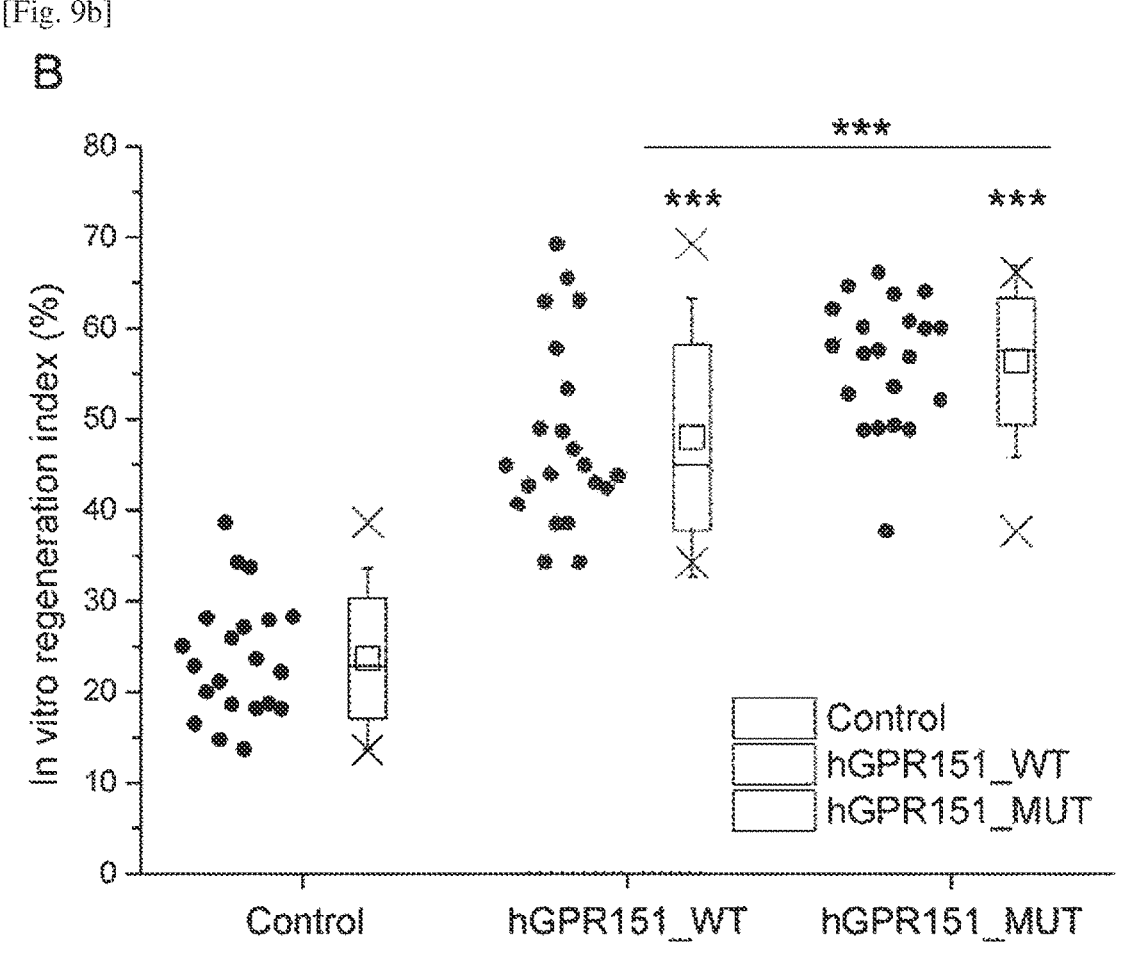

SEQUENCE LISTING

<160> NUMBER OF SEQ ID NOS: 19

<210> SEQ ID NO 1
<211> LENGTH: 46
<212> TYPE: RNA
<213> ORGANISM: Artificial Sequence
<220> FEATURE:
<223> OTHER INFORMATION: Gpr151 5'UTR_human (hGpr151_WT)

-continued

<400> SEQUENCE: 1
caaaccuaaa uaagaaucua acuucuguaa gaagcuguga agagug                         46

<210> SEQ ID NO 2
<211> LENGTH: 41
<212> TYPE: RNA
<213> ORGANISM: Artificial Sequence
<220> FEATURE:
<223> OTHER INFORMATION: Gpr151 5'UTR_rat

<400> SEQUENCE: 2
accaaccuaa uaagaagcua acaucugcag ggaggagcug g                              41

<210> SEQ ID NO 3
<211> LENGTH: 41
<212> TYPE: RNA
<213> ORGANISM: Artificial Sequence
<220> FEATURE:
<223> OTHER INFORMATION: Gpr151 5'UTR_mouse

<400> SEQUENCE: 3
ccaaccuaaa caagaagcua ccaucugcag ggaggagcuu g                              41

<210> SEQ ID NO 4
<211> LENGTH: 35
<212> TYPE: RNA
<213> ORGANISM: Artificial Sequence
<220> FEATURE:
<223> OTHER INFORMATION: Gpr151 5'UTR_?CSDE1

<400> SEQUENCE: 4
ccaaccuaaa gcuaccaucu gcagggagga gcuug                                     35

<210> SEQ ID NO 5
<211> LENGTH: 32
<212> TYPE: RNA
<213> ORGANISM: Artificial Sequence
<220> FEATURE:
<223> OTHER INFORMATION: Gpr151 5'UTR_4X mutant

<400> SEQUENCE: 5
acaagaagac aagaagacaa gaagacaaga ag                                        32

<210> SEQ ID NO 6
<211> LENGTH: 11
<212> TYPE: RNA
<213> ORGANISM: Artificial Sequence
<220> FEATURE:
<223> OTHER INFORMATION: Gpr151 5'UTR_h (mouse)

<400> SEQUENCE: 6
ccaaccuaaa c                                                               11

<210> SEQ ID NO 7
<211> LENGTH: 41
<212> TYPE: RNA
<213> ORGANISM: Artificial Sequence
<220> FEATURE:
<223> OTHER INFORMATION: Gpr151 5'UTRm

<400> SEQUENCE: 7
ccaaccuaaa caagaagcua ccaucugcag ggaggucgaa g                              41

<210> SEQ ID NO 8

-continued

```
<211> LENGTH: 18
<212> TYPE: RNA
<213> ORGANISM: Artificial Sequence
<220> FEATURE:
<223> OTHER INFORMATION: Gpr151 5'UTR?

<400> SEQUENCE: 8
ccaaccuaaa caagaagc                                                      18

<210> SEQ ID NO 9
<211> LENGTH: 35
<212> TYPE: RNA
<213> ORGANISM: Artificial Sequence
<220> FEATURE:
<223> OTHER INFORMATION: Gpr151 5'UTR?CSDE1

<400> SEQUENCE: 9
ccaaccuaaa gcuaccaucu gcagggaggu cgaag                                   35

<210> SEQ ID NO 10
<211> LENGTH: 46
<212> TYPE: RNA
<213> ORGANISM: Artificial Sequence
<220> FEATURE:
<223> OTHER INFORMATION: hGpr151_MUT

<400> SEQUENCE: 10
caaaccuaaa uaagaaucua acuucuguaa gaaggacuga agagug                       46

<210> SEQ ID NO 11
<211> LENGTH: 21
<212> TYPE: DNA
<213> ORGANISM: Artificial Sequence
<220> FEATURE:
<223> OTHER INFORMATION: Gpr151-targeting shRNA

<400> SEQUENCE: 11
gcaaagattt ctgctttcaa a                                                  21

<210> SEQ ID NO 12
<211> LENGTH: 21
<212> TYPE: DNA
<213> ORGANISM: Artificial Sequence
<220> FEATURE:
<223> OTHER INFORMATION: Csde1-targeting shRNA

<400> SEQUENCE: 12
tgctgtaagt gctcgtaata t                                                  21

<210> SEQ ID NO 13
<211> LENGTH: 21
<212> TYPE: DNA
<213> ORGANISM: Artificial Sequence
<220> FEATURE:
<223> OTHER INFORMATION: Khdrbs1-targeting shRNA

<400> SEQUENCE: 13
gcatgtcttc attgaagtct t                                                  21

<210> SEQ ID NO 14
<211> LENGTH: 20
<212> TYPE: DNA
<213> ORGANISM: Artificial Sequence
<220> FEATURE:
<223> OTHER INFORMATION: Gpr151 Forward primer

<400> SEQUENCE: 14
```

-continued

```
ctgggtttgc cgacaccaat                                                   20

<210> SEQ ID NO 15
<211> LENGTH: 21
<212> TYPE: DNA
<213> ORGANISM: Artificial Sequence
<220> FEATURE:
<223> OTHER INFORMATION: Gpr151 Reverse primer

<400> SEQUENCE: 15
agagagacgg aatgatggtc c                                                 21

<210> SEQ ID NO 16
<211> LENGTH: 20
<212> TYPE: DNA
<213> ORGANISM: Artificial Sequence
<220> FEATURE:
<223> OTHER INFORMATION: Jun Forward primer

<400> SEQUENCE: 16
ccttctacga cgatgccctc                                                   20

<210> SEQ ID NO 17
<211> LENGTH: 22
<212> TYPE: DNA
<213> ORGANISM: Artificial Sequence
<220> FEATURE:
<223> OTHER INFORMATION: Jun Reverse primer

<400> SEQUENCE: 17
ggttcaaggt catgctctgt tt                                                22

<210> SEQ ID NO 18
<211> LENGTH: 23
<212> TYPE: DNA
<213> ORGANISM: Artificial Sequence
<220> FEATURE:
<223> OTHER INFORMATION: Atf3 Forward primer

<400> SEQUENCE: 18
gaggattttg ctaacctgac acc                                               23

<210> SEQ ID NO 19
<211> LENGTH: 21
<212> TYPE: DNA
<213> ORGANISM: Artificial Sequence
<220> FEATURE:
<223> OTHER INFORMATION: Atf3 Reverse primer

<400> SEQUENCE: 19
ttgacggtaa ctgactccag c                                                 21
```

TREATMENT OF NERVE DAMAGE USING 5'UTR OF Gpr151 GENE OR VARIANT THEREOF

REFERENCE TO AN ELECTRONIC SEQUENCE LISTING

The contents of the electronic sequence listing PPP20235761US sequence listing revised.txt; Size: 4,293 bytes; and Date of Creation: Jul. 15, 2024) is herein incorporated by reference in its entirety. The contents of the electronic sequence listing in no way introduces new matter into the specification.

BACKGROUND OF THE INVENTION

Field of the Invention

Disclosed is a composition for treating a neurological disease caused by nerve injury, including an isolated polynucleotide of a 5'-untranslated region (5'UTR) of a Gpr151 gene or a variant thereof. Also disclosed are a novel variant polynucleotide of 5'UTR of a Gpr151 gene and a vector including the polynucleotide.

Description of the Related Art

Injury of the central nervous system may cause semipermanent loss of functions, which may lead to paralysis or death. In addition, injury of peripheral nerves caused by various causes, such as physical injury or anticancer drugs, may lead to neurodegeneration or neuronal death because nerve regeneration capacity is remarkably reduced. However, there is almost no method or material that can prevent or treat nerve injury or accelerate the recovery rate so far.

Therefore, there is a need for the development of a substance that can promote axon regrowth and nerve regeneration after injury of the central and/or peripheral nerves.

SUMMARY OF THE INVENTION

One embodiment provides a use of an isolated 5'-untranslated region (5'UTR) polynucleotide of a Gpr151 gene, a variant thereof, or a DNA encoding the 5'UTR polynucleotide or the variant for treating a neurological disease caused by nerve injury, a treatment composition, and/or a treatment method therefor.

Another embodiment provides a use of an isolated 5'UTR polynucleotide of a Gpr151 gene, a variant thereof, or a DNA encoding the 5'UTR polynucleotide or the variant for promoting nerve regeneration, a composition, and/or a method therefor.

Still another embodiment provides a novel 5'UTR polynucleotide variant of a Gpr151 gene.

Yet another embodiment provides a vector including the novel 5'UTR polynucleotide variant or a DNA encoding the same.

BRIEF DESCRIPTION OF THE DRAWINGS

The accompanying drawings are intended to explain the contents of the present invention in more details to those skilled in the art, but the technical principle of the present invention is not limited thereto.

FIG. 1: The results show that Gpr151 is an injury-responsive protein-coding gene that is not directed to ribosome. (A) Advillin promoter-based Cre recombinase-expressing (Advillin-Cre) mice were crossed with RiboTag mice (Rp122HA) to produce mice that express hemagglutinin (HA) epitope-tagged RPL22 particularly in dorsal root ganglia (DRG). The image shows representative immunohistochemical data of L A DRG sections immunostained with anti-HA antibody (green) and TUJ1-antibody (red). Scale bar, 100 μm. (B) Illustration of experimental scheme of a comparative analysis between differential gene expression (DEG) and ribosome-binding efficiency. IP represents immunoprecipitation, and HA represents HA-epitope and anti-HA antibody. (C) A three-dimensional plot in which the x-axis represents [Ribo], $\Delta$=reads@injured−reads@uninjured and the y-axis represents $\log_2$-transformed reads@injured/reads@uninjured. The size of circle indicates the relative expression level 24 hours after injury. (D) A list of DEGs in which $\log_2$[FC] is higher than 1.5 in (C) represented by color codes defined by the [Ribo] value. The green box represents the size of circle in (C). The number represents the y value. The genes indicated by the boxes represent single-exon genes. (E) Results of a Western blot analysis from L4,5 DRGs tissues with (+injury) or without (−injury) sciatic nerve axotomy. The cases represent independent biological replicates. GPR151 indicates an anti-GPR151 antibody, GAPDH indicates an anti-GAPDH antibody, and c-Jun indicates an anti-c-Jun antibody. (F) The log10-converted relative RNA and protein levels determined by RT-qPCR (RNA) and Western blot (protein), respectively (n=3; mean±SEM; *p<0.05, ***p<0.001, by t-test, respectively). (G) Results of a fluorescence in situ hybridization (FISH) analysis and DAPI labeling (blue) of L4 DRG sections prepared at 24 hours after sciatic nerve axotomy with probes to Gpr151 (green) and Gapdh (red). Scale bar, 5 μm. (H) The image shows representative immunohistochemistry of the L4 DRG sections prepared at 24 hours after sciatic nerve axotomy and immunostained with an anti-GPR151 antibody (green) and an anti-TUJ1 tubulin antibody (red). Scale bar, 100 μm.

FIG. 2: The results show that Gpr151 mRNA is required for axon regeneration, and Gpr151 protein negatively regulates axon growth. (A) Results of in vitro axon regeneration analysis of embryonic DRG neurons. Controls, Gpr151-KD (knockdown), Gpr151-KD (5'UTR-CDSm) overexpressing Gpr151-5'UTR-AUC variant, and Gpr151-KD (5'UTR-CDSw) overexpressing Gpr151-5'UTR-AUG wild type. Scale bar, 100 μm. (B) Schematic diagram of Gpr151-constructs of CDSm and CDSw. AUC and AUG represent the start codons of the protein-coding sequence (CDS). 5'UTR represents a 5'-untranslated region of a Gpr151 gene. (C) Western blot analysis results validating the overexpression levels of CDSm and CDSw constructs shown in (B). An anti-FLAG epitope antibody was used for the Western blot analysis. (D) Statistical analysis results of (A). Average of the relative axon length (n=67, 63, 67, 62 for each condition; ***p<0.001, #p=0.05, by ANOVA and Tukey test). (E) Cumulative frequency of (A). (F) Results of an in vitro axon regeneration analysis of embryonic DRG neurons. Controls (denoted as control), 5'UTR of Gpr151 overexpression (denoted as 5'UTR), protein-coding sequence overexpression (denoted as CDS), and Gpr151-knockdown (denoted as KD). (G) Statistical analysis results of (F). Average of the relative axon length (n=160, 147, 267, 161 cells for each condition; *p<0.05, ***p<0.001, by ANOVA and Tukey test).

FIG. 3: The results show that Gpr151 protein-null mice expressing partial Gpr151 mRNA exhibit enhanced regeneration capacity. (A) A schematic diagram of the Gpr151 gene in control or targeted knockout (KO) mice. (B) Average fold change in normal or variant Gpr151 mRNA levels one or three days after sciatic nerve axotomy (n=3 for each; *p<0.05, ns, not significant, by ANOVA and Tukey test). (C) Results of an in vivo axon regeneration analysis. Sciatic nerves from the controls or Gpr151 protein-null mice (KO) were crushed and dissected three days after injury and immunostained with an anti-SCG10 antibody and a TUJ1 antibody. Scale bar, 500 μm. (D and E) Regeneration index from (C) (n=7 for control, n=5 for KO; *p<0.05, by t-test; mean±SEM). (F) Adult DRG neurons cultured to monitor neuronal pre-conditioning effects. Mouse L4-5 DRG tissue was dissected and plated three days after sciatic nerve axotomy (+injury). Scale bar, 100 μm. (G) Average of the longest axon length from (F) (3 mice for each condition, 304, 313, 291, 283 cells for each condition; ***p<0.001, ANOVA and Tukey test). (H) Cumulative frequency of the longest axon length from (F). (I) Percentage (%) of neurons in the three categories of the longest axon length.

FIG. 4: The results showed that CSDE1 interacts with the 5'UTR of Gpr151 to negatively regulate axon regeneration. (A) Coomassie staining results of SDS-PAGE of 5'UTR-binding protein. (B) 5'UTR sequence alignment of mouse, rat and human GPR 151 genes. The green box represents nAAGnA, which is a CSDE1-binding consensus motif, and the yellow shade represents the start codon of Gpr151 CDS. (C) Results of a Western blot analysis of 5'UTR pull-down assay. (D) Relative folds of Gpr151 mRNA analyzed by RT-qPCR (n=3, *p<0.001, nd, not determined by t-test; mean±SEM). (E) Artificial RNA sequence of ΔCSDE1 or 4× variant. (F) Western blot analysis results of pull-down assay using bait, ΔCSDE1, or 4× variant. (G) Results of a Western blot analysis of a pull-down assay using bait, mouse GPR151 5'UTR, or human GPR15 5'UTR. (H) Results of in vitro axon regeneration assays of control, CSDE1 knock-down (shCSDE1) and KHDRBS1 knockdown (shKHDRBS1) embryonic DRG. Scale bar, 100 μm. (I) Results of a statistical analysis of axon length regeneration of (H) (n=254, 198, 167 for control, shCSDE1, and shKHDRBS1; *p<0.001, ns, not significant by ANOVA and Tukey test) (mean±SEM). (J) Secondary structure of the 5'UTR of Gpr151 wild type (5'UTR$_{WT}$), structure of a variant without a CSDE1-binding motif (h), and structure of a variant with a single-stranded CSDE1-binding motif (5'UTRm), structure of a stemless variant (Δ). (K) Western blot analysis results of a pull-down assay using bait of (J). (L and M) Western blot analysis results of a pull-down assay using competitor Δ for mouse and human 5'UTR.

FIG. 5: The results show that expression of the engineered 5'UTR of Gpr151 mRNA regulates CSDE1-RNA interactions and RNA groups associated with distinct biological processes are dissociated. (A) Results of an in vitro axon regeneration assay of embryonic DRG neurons expressing a control vector, the 5'UTR of Gpr151 (5'UTR$_{WT}$), or a variant 5'UTR with a single-stranded CSDE1-binding motif (5'UTRm). Scale bar, 100 μm. (B) Results of a statistical analysis of relative average axon length from (A) (n=97, 104, 98 cells for control, 5'UTR$_{WT}$, and 5'UTRm; *p<0.05, ***p<0.001 by ANOVA and Tukey test; mean±SEM). (C) A Two-dimensional plot of the x- and y-axes of the log2-transformed fold change of [reads@5'UTRm/ reads@control]. (D and E) Results of a gene ontology analysis (D) and KEGG pathway analysis (E) of genes dissociated from CSDE1 by 5'UTRm overexpression, shown in the green box at the top of (C). (F) Proteomic analysis of antibody array results in which the x-axis represents the log2-transformed values normalized in control and the y-axis represents the log2-transformed values normalized in 5'UTRm. Red and blue represent target proteins upregulated or downregulated by 30% or more, respectively. Percentages (%) represent the relative proportions of the colored targets to a total of 1,358 probes. (G) Target proteins in (F) plotted against their corresponding CSDE1-dissociation factor of the mRNAs and negative log2-transformed fold change [reads@5'UTRm/reads@control].

FIG. 6: The results show that in vivo gene delivery of an engineered 5'UTR of Gpr151 mRNA promoted axon regeneration in the sciatic nerve and optic nerve. (A) Experiment timeline of in vivo gene delivery for analyzing in vivo regeneration in the mouse sciatic nerve (wk, weeks). (B and C) In vivo regeneration from (D) (n=8 for control, n=10 for 5'UTRm; *p<0.05, #p<0.001 by t-test; mean±SEM). (D) Results of an in vivo axon regeneration analysis in the sciatic nerve. Representative longitudinal sections of sciatic nerves from control or 5'UTRm-expressing mice are shown. The red dotted arrow indicates the area of injury. Scale bar, 500 μm. (E) Experiment timeline of in vivo gene delivery for analyzing in vivo axon regeneration in the mouse optic nerve (wk, weeks). (F) Representative longitudinal sections of optic nerves from control or 5'UTRm-expressing mice are shown. The red dotted arrow indicates the area of injury. Scale bar, 200 μm. (G) Estimated number of regenerating axons (n=5 for control, n=6 for 5'UTRm; *p<0.05, *p<0.001 by t-test; mean±SEM). (H) Results of a qPCR analysis of Gpr151 and Atf3 in mouse retina with injury (+injury) or without injury (−injury) (n=3 for each condition; *p<0.001, ns, not significant by t-test, mean±SEM,).

FIG. 7: Results of an in vitro axon regeneration assay. (A) Representative images of control, 5'UTRm-overexpressing and 5'UTRm ΔCSDE1-overexpressing embryonic DRG neurons are shown. Scale bar, 100 μm. (B) Results of a statistical analysis of axon length regeneration of (A) (n=254, 198, 167 for control, shCSDE1, and shKHDRBS1; ***p<0.001, ns, not significant by ANOVA and Tukey test); mean±SEM. (B) Average statistics of relative axon length of (A) (n=64, 55, 68 cells for control, 5'UTRm, 5'UTRm ΔCSDE1; *p<0.05, ns by ANOVA and Tukey test) mean±SEM). Related to FIG. 5A.

FIG. 8: Secondary structure of a 5'UTR of human Gpr151 wild type (hGPR151_WT) and a structure of a variant in which the CSDE1-binding motif is single-stranded (hGPR151_MUT).

FIG. 9: Results of an in vitro axon regeneration assay for the 5'UTR of human Gpr151 and variants thereof. (A) Immunofluorescence staining results of embryonic DGR neurons infected with control (pLKO.1 null vector), hGPR151_WT (pLKO.1-hGPR151_WT), or hGPR151_MUT (pLKO.1-hGPR151_MUT). (B) Results of a statistical analysis for the regeneration index calculated from (A) (The square represents the arithmetic mean, X represents the standard deviation, and dots represent individual measurement values. ***p<0.001 by one-way ANOVA with Tukey test.)

DETAILED DESCRIPTION OF THE EMBODIMENTS

As one embodiment, provided is a composition for treating a neurological disease caused by nerve injury, including an isolated 5'-untranslated region (5'UTR) polynucleotide of a Gpr151 gene, a variant thereof, or a DNA encoding the 5'UTR polynucleotide or variant, wherein the variant includes nAAGmA in a wild-type sequence of 5'UTR of a Gpr151 gene, wherein n is c, g or u, and m is a, u or g.

In one preferred embodiment, the polynucleotide may be derived from a mammal.

The polynucleotide may have a nucleic acid sequence of SEQ ID NO: 1 (mouse), SEQ ID NO: 2 (rat) or SEQ ID NO: 3 (human).

The variant may further satisfy one or more of the following (a) to (d): (a) having 85% or higher sequence identity with a wild-type sequence of 5'UTR of a Gpr151 gene and exhibiting nerve regeneration activity; (b) the nAAGmA being single-stranded and the variant exhibiting nerve regeneration activity; (c) including no stem-loop region and exhibiting nerve regeneration activity; and (d) all or a part of a 5' direction and/or 3' direction sequence of the nAAGmA being deleted and the variant exhibiting nerve regeneration activity.

The variant may have a nucleic acid sequence of SEQ ID NO: 7, SEQ ID NO: 8, or SEQ ID NO: 10.

The polynucleotide, variant, or DNA may be included in a vector.

The vector may be an adeno-associated viral vector (AAV), an adenoviral vector, a retroviral vector, a lentiviral vector, a herpes simplex virus vector, or an alphavirus vector.

The neurological disease caused by nerve injury may be a central nervous system (CNS) disease or a peripheral nervous system (PNS) disease.

The neurological disease caused by nerve injury is Alzheimer's disease, dementia, multi-infarct dementia, frontotemporal dementia, dementia with Lewy bodies, mild cognitive impairment, corticobasal degeneration, Parkinson's disease, depression, metabolic brain disease, multiple systemic atrophy Multiple system atrophy, Huntington's disease, Pick's disease, progressive supranuclear palsy, epilepsy, dentatorubropallidoluysian atrophy, spinocerebellar ataxia, glaucoma, stroke, brain ischemia, demyelinating disease, post-encephalitic parkinsonism, Tourette's syndrome, restless legs syndrome legs syndrome), attention deficit disorders with hyperactivity, spinal muscular atrophy, spinal bulbar muscular atrophy, amyotrophic lateral sclerosis (ALS), multiple sclerosis, primary lateral sclerosis, progressive bulbar palsy, paralysis, spinal cord injury, optic nerve injury, traumatic brain injury, diffuse axonal injury, or peripheral nerve trauma.

As another embodiment, provided is a treatment method of a neurological disease caused by nerve injury, including a step of administering an isolated 5'UTR polynucleotide of a Gpr151 gene, a variant thereof, or a DNA encoding the 5'UTR polynucleotide or variant to a subject, wherein the variant includes nAAGmA in a wild-type sequence of 5'UTR of a Gpr151 gene, wherein n is c, g or u, and m is a, u or g.

As still another embodiment, provided is a nerve regeneration promoting method, including a step of administering an isolated 5'UTR polynucleotide of a Gpr151 gene, a variant thereof, or a DNA encoding the 5'UTR polynucleotide or variant to a subject, wherein the variant includes nAAGmA in a wild-type sequence of 5'UTR of a Gpr151 gene, wherein n is c, g or u, and m is a, u or g.

As yet another embodiment, provided is an isolated 5'UTR polynucleotide of a Gpr151 gene, a variant thereof, or a DNA encoding the 5'UTR polynucleotide or variant for use in treatment of a neurological disease caused by nerve injury, wherein the variant includes nAAGmA in a wild-type sequence of 5'UTR of a Gpr151 gene, wherein n is c, g or u, and m is a, u or g.

As yet another embodiment, provided is an isolated 5'UTR polynucleotide of a Gpr151 gene, a variant thereof, or a DNA encoding the 5'UTR polynucleotide or variant for use in nerve regeneration promotion, wherein the variant includes nAAGmA in a wild-type sequence of 5'UTR of a Gpr151 gene, wherein n is c, g or u, and m is a, u or g.

As yet another embodiment, provided is an isolated polynucleotide consisting of a nucleic acid sequence of SEQ ID NO: 7 or SEQ ID NO: 10.

As yet another embodiment, provided is a vector including the polynucleotide of or DNA encoding the same.

Hereinafter, the present invention will be described in more detail.

The terms "5'UTR" or "5'-untranslated region" or "5'UTR polynucleotide" are used interchangeably and refer to a region positioned at a 5' (i.e. upstream) of a coding sequence of an mRNA and not translated into a protein. Generally, 5'UTR is defined as a region between the transcription start site of and a start codon of an mRNA. A 5'UTR of a mammalian mRNA may have a base length of tens to hundreds of bases. A 5'UTR may include a regulatory element to control gene expression, for example, a regulatory element may be a ribosome binding site (RBS).

Generally, a process of translating an mRNA into a protein begins with binding of a 30S subunit of a ribosome to a 5'UTR. Specifically, translation into a protein begins when a 16S rRNA (16S ribosomal RNA) within a 30S subunit of a ribosome binds to a ribosome binding site in a 5'UTR and a tRNA recognizes and binds to a start codon (AUG) of the mRNA.

Conventionally, it has been recognized that as the level of mRNA increases, the level of protein increases accordingly, and at this time, a 5'UTR of an mRNA may contribute to regulating the expression (translation) of main coding sequences. In this respect, a protein-coding differentially expressed gene (DEG) assay has been considered as a reliable approach to study the underlying mechanisms of cellular responses to stimuli, for example, axon regeneration after injury. However, several recent studies have shown a low correlation between mRNAs and protein levels, suggesting that studies of differentially expressed mRNAs themselves, independent of protein functions, are required.

Accordingly, in a DEG analysis, the present inventors identified a group of mRNAs upregulated by nerve injury in which ribosome binding is not strongly associated with transcriptional regulation. In addition, the present inventors found that Gpr151, an injury-induced coding gene, promotes axon regeneration through a non-coding function of the 5'-URT (Gpr151-5'UTR). It was confirmed that Gpr151-5'UTR interacts with CSDE1, a stress-responsive RNA-binding protein (RBP) and changes a CSDE1-binding RNA pool. Furthermore, it was confirmed that in addition to a wild-type Gpr151-5'UTR, introduction of a Gpr151-5'UTR variant engineered to have stronger CSDE1 binding promotes axon regeneration both in vitro and in vivo.

More specifically, in the present invention, a comparative analysis of transcriptomes was conducted under an axon regeneration paradigm based on their ribosome-binding efficiency using RiboTag mice after axonal injury. As a result, it was found that a group of injury-responsive genes exhibited no increase in their ribosome-binding efficiency even when their mRNA was drastically upregulated after axonal injury. Of these genes, Gpr151 encodes an orphan G protein-coupled receptor (GPCR) associated with neuropathic pain and nicotine addiction. Because Gpr151 is a single-exon protein-coding gene, without a need to consider alternatively spliced isoforms, the mRNA function may be studied by performing an experiment with a single form of transcript. In the present invention, it was confirmed that the 5'UTR of Gpr151 mRNA promotes axon regeneration, CSDE1 was identified as an RBP interacting with the 5'UTR, and CSDE1 was found to be a negative regulator of axonal regrowth in vitro. In addition, a variant in which a part of the Gpr151-5'UTR sequence was prepared to have strong CSDE1 binding, and it was found that expressing the 5'UTR showed enhanced CSDE1-binding and enhanced axon regeneration both in vitro and in vivo. It was confirmed that overexpression of the 5'UTR variant did not significantly change the transcriptomic profiles but modulated the pool of CSDE1-bound RNA and promoted the release of RNA from CSDE1, thereby inhibiting the functions of CSDE1.

Accordingly, the present invention provides a use, a composition, and a method for treating a neurological disease, using an isolated 5'UTR polynucleotide of a Gpr151 gene, a variant thereof, or a DNA encoding the 5'UTR polynucleotide or variant. In addition, the present invention provides a use, a composition, and a method for promoting nerve regeneration, using an isolated 5'UTR polynucleotide of a Gpr151 gene, a variant thereof, or a DNA encoding the 5'UTR polynucleotide or variant.

The term "polynucleotide" is used synonymously with "nucleic acid" or "nucleic acid molecule" and refers to a deoxyribonucleotide or ribonucleotide or a polymer thereof in a single-or double-stranded form.

The term "isolated" refers to something that is separated from a natural environment, or manufactured or obtained artificially. For example, a nucleic acid sequence in an original state within a natural host is not "isolated," but a polynucleotide of the same sequence that has been separated from a coexisting material in a natural state or produced recombinantly is "isolated." Furthermore, a polynucleotide introduced into an organism by transformation, genetic manipulation, or any other recombinant method is "isolated" even though it is present within an organism.

The term "isolated 5'UTR polynucleotide of a Gpr151 gene" refers to a 5'UTR region in an mRNA of the Gpr151 gene, more specifically, a region between a transcription start site and a start codon, which is a 5'-end of the mRNA of the Gpr151 gene. (i.e., a region from a 5'-terminal base to a base immediately before the start codon), and preferably refers to a polynucleotide having a wild-type sequence of the 5'UTR of the Gpr151 gene.

The term "wild-type sequence" is used interchangeably with "natural sequence" and refers to a sequence of polynucleotide isolated from a naturally occurring source.

The term "variant" is intended to refer to a nucleic acid variant having a nucleic acid sequence that differs from an original sequence by deletion, substitution, insertion, addition, and/or inversion of one or more bases in a reference nucleic acid sequence (e.g., wild-type sequence).

Specifically, a variant of the present invention includes a consensus CSDE1-binding motif, nAAGmA, (here n is c, g or u, and m is a, u or g). For example, the consensus CSDE1-binding motif is UAAGAA for human Gpr151-5'UTR, CAAGAA for mouse, and UAAGAA for rat, each positioned +11 to +16 from a transcription start site (see FIG. 4B). Through an embodiment in the present invention, it was confirmed that the consensus CSDE1-binding motif sequence in Gpr151-5'UTR is important for interaction with CSDE1 and that when this sequence is deleted, binding to CSDE1 is significantly destabilized (FIGS. 4F and 4K) and axon regeneration ability was reduced (FIG. 7).

Therefore, in one preferred embodiment, a variant in the present invention includes nAAGmA in a wild-type sequence of a 5'UTR of a Gpr151 gene (where n is c, g, or u, and m is a, u, or g).

In another preferred embodiment, a variant in the present invention may include nAAGmA in a wild-type sequence of a 5'UTR of a Gpr151 gene (where n is c, g or u and m is a, u or g), and further satisfy one or more of (a) to (d):

(a) having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or higher sequence identity with a wild-type sequence of 5'UTR of a Gpr151 gene and the variant exhibiting nerve regeneration activity;

(b) the nAAGmA being single-stranded (for example, a part or all of the nAAGmA gene forming no stem-loop region) and the variant exhibiting activity equivalent to a wild-type sequence of 5'UTR of a Gpr151 gene, for example, nerve regeneration activity;

(c) including no stem-loop region and exhibiting activity equivalent to a wild-type sequence of 5'UTR of a Gpr151 gene, for example, nerve regeneration activity; and (d) all or a part of a 5' direction and/or 3' direction sequence of the nAAGmA being deleted and the variant exhibiting activity equivalent to a wild-type sequence of 5'UTR of a Gpr151 gene, for example, nerve regeneration activity.

"Percent (%) identity" of a sequence refers to the degree to which bases are identical when two or more polynucleotide sequences are aligned to match each other as much as possible and then the sequences are compared. Percent sequence identity is calculated by, for example, comparing two optimally aligned sequences across a comparison region and determining the number of positions where identical amino acid or nucleic acid appears in both sequences to obtain the number of matched positions, dividing the number of matched positions by a total number of positions within the comparison range (i.e., range size), and multiplying the result value by 100 to obtain the percentage of sequence identity. The percent sequence identity may be determined using a known sequence comparison software program, examples of which include BLASTN (NCBI), CLC Main Workbench (CLC bio), and MegAlignTM (DNASTAR Inc).

The term "motif" refers to a pattern within a biological molecule or a pattern of subunits thereof. For example, the term "motif" may be used in association with a pattern of subunits of a non-coding biological molecule, or a pattern of subunits of a coded embodiment of a biological molecule.

In a preferred embodiment, an isolated 5'UTR polynucleotide of a Gpr151 gene may be derived from a mammal. Examples of such mammals include primates, including humans, monkeys, chimpanzees, or other apes; livestock animals including cows, horses, sheep, goats, and pigs; domestic animals including rabbits, dogs, and cats; or rodents including rats, mice, and guinea pigs, but are not limited thereto.

Specifically, a 5'UTR polynucleotide may have a nucleic acid sequence of SEQ ID NO: 1 (mouse), SEQ ID NO: 2 (rat), or SEQ ID NO: 3 (human), and a variant thereof may have a nucleic acid sequence of SEQ ID NO: 7 (5'UTRm) or SEQ ID NO: 8 (5'UTRA) or SEQ ID NO: 10 (hGPR151_MUT).

A polynucleotide or variant thereof, or DNA encoding them of the present invention may be combined with any gene delivery technology known in the art for efficient delivery. For example, the polynucleotide or variant thereof, or DNA encoding them, may be administered and delivered when it is included in a vector. A vector may be a plasmid or viral vector. A viral vector may be an RNA viral vector or a DNA viral vector, for example, an adeno-associated viral vector (AAV), an adenoviral vector, a retroviral vector, a lentiviral vector, a herpes simplex virus vector, or an alphavirus vector. However, it is not limited thereto, and any viral vector known in the art may be used.

An AAV may be serotype 1 (AAV1), AAV2, AAV3 (including AAV3A and AAV3B), AAV4, AAV5, AAV6, AAV7, AAV8, AAV9, AAV10, AAV11, AAV12, AAV-DJ, AAVrh10, AAVLK03, AAVhu37, AAVrh64R1, or Anc 80, but is not limited thereto. An AAV typically include a transgene and regulatory sequences thereof, and 5' and 3' AAV inverted terminal repeats (ITRs). The transgene is a nucleic acid sequence that is heterologous to a vector sequence and generally encodes a target polypeptide, protein, functional RNA molecule, or other gene product.

In one embodiment, a vector may include an expression regulatory sequence that allows a corresponding polynucleotide, variant, or DNA to be expressed. Examples of an expression regulatory sequence may include appropriate transcription initiation, termination, promoter, and enhancer sequences; efficient RNA processing signals, for example, splicing and polyadenylation (poly A) signals; or sequences that stabilize cytoplasmic mRNA, but are not limited thereto. A large number of expression regulatory sequences, including promoters that are original, constitutive, inducible and/or tissue-specific, are known in the art and may be utilized. A polynucleotide sequence and a regulatory sequence are referred to as being "operably" linked when they are covalently linked in a manner such that expression or transcription of the polynucleotide sequence is placed under the influence or regulation of the regulatory sequence.

In another embodiment, for introduction of a composition of the present invention including a polynucleotide, variant, or DNA, delivery vehicles such as liposomes, exosomes, nanoparticles, microparticles, microspheres, lipid particles, microvesicles, cationic polymers, cationic peptides, and cationic lipids may be used. For example, when delivered through a vector, a polynucleotide, variant, or DNA of the present invention may be formulated by being encapsulated in any one of liposomes, exosomes, nanoparticles, microparticles, microspheres, lipid particles, microvesicles, cationic polymers, cationic peptides, and cationic lipids, but is not limited thereto.

Since a composition of the present invention is effective in regenerating nerves after nerve injury, it may be used for the prevention or treatment of a neurological disease caused by nerve injury or accompanied by nerve injury, or a neurological disease treatable by nerve regeneration. Specifically, the neurological disease may be a CNS disease or a PNS disease.

More specifically, the neurological disease may be Alzheimer's disease, dementia, multi-infarct dementia, frontotemporal dementia, dementia with Lewy bodies, mild cognitive impairment, corticobasal degeneration, Parkinson's disease, depression, metabolic brain disease, multiple systemic atrophy Multiple system atrophy, Huntington's disease, Pick's disease, progressive supranuclear palsy, epilepsy, dentatorubropallidoluysian atrophy, spinocerebellar ataxia, glaucoma, stroke, brain ischemia, demyelinating disease, post-encephalitic parkinsonism, Tourette's syndrome, restless legs syndrome legs syndrome), attention deficit disorders with hyperactivity, spinal muscular atrophy, spinal bulbar muscular atrophy, amyotrophic lateral sclerosis (ALS), multiple sclerosis, primary lateral sclerosis, progressive bulbar palsy, paralysis, spinal cord injury, optic nerve injury, traumatic brain injury, diffuse axonal injury, or peripheral nerve trauma, but is not limited thereto.

Administration of a composition of the present invention may prevent a disease, or inhibit, discontinue, or delay the onset or progression of pathological conditions, or improve or beneficially modify symptoms.

The term "effective amount" refers to an amount sufficient to achieve a desired outcome when administered to a subject, including humans, for example, an amount effective in treating or preventing a neurological disease. An effective amount may vary according various factors such as the level of polynucleotide expression required to achieve a therapeutic effect, the stability of a polynucleotide product, a formulation method, the mode of administration, the patient's age, weight, sex, severity of the disease, food, time of administration, route of administration, rate of excretion, and response. Dose or treatment use may be adjusted to provide optimal therapeutic response as understood by those skilled in the art.

A composition of the present invention may be provided with one or more additives selected from the group consisting of pharmaceutically acceptable carriers, diluents, and excipients.

The pharmaceutically acceptable carrier is one that is commonly used in formulation and may include, for example, one or more selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like, but is not limited thereto. In addition to the above ingredients, the composition may further include one or more selected from the group consisting of diluents, excipients, lubricants, wetting agents, sweeteners, flavoring agents, emulsifiers, suspending agents, preservatives, and the like. In addition to the examples described above, pharmaceutically acceptable carriers and preparations suitable for the present invention are described in detail in a document [Remington's Pharmaceutical Sciences, latest version].

The composition may be administered orally or parenterally. When administered parenterally, it may be administered by intravenous injection, subcutaneous injection, intramuscular injection, intraperitoneal injection, endothelial administration, topical administration, intranasal administration, intraocular administration, intramedullary administration, intrathecal administration, intracranial administration, intrastriatal administration, and the like.

In some embodiments, the composition may be provided as a sterile liquid formulation, for example, as an isotonic aqueous solution, suspension, emulsion, dispersion or viscous composition, which in some aspects may be buffered to a selected pH. Liquid formulations are generally easier to prepare than gels, other viscous compositions, and solid compositions. In addition, liquid compositions are particularly convenient to administer by injection. Meanwhile, viscous compositions may be formulated within an appropriate viscosity range to provide a longer period of contact with a particular tissue. Liquid or viscous compositions may include a carrier, which may be, for example, a solvent or dispersion medium containing water, saline, phosphate buffered saline, polyols (e.g., glycerol, propylene glycol, liquid polyethylene glycol), and a suitable mixture thereof.

Sterile injectable solutions may be prepared by incorporating a binding molecule in a solvent such as a suitable carrier, diluent, or admixture with excipients such as sterile water, saline, glucose, dextrose, or the like. The composition may also be freeze-dried. The composition may contain auxiliary substances such as wetting agents, dispersing agents or emulsifiers (e.g., methylcellulose), pH buffering agents, gelling or viscosity-enhancing additives, preservatives, flavoring agents, colorants, or the like depending on the route of administration and desired manufacturing route.

Various additives may be added to improve the stability and sterilization properties of the composition, including antibacterial preservatives, antioxidants, chelating agents, and buffers. Prevention of microbial actions may be ensured by various antibacterial and antifungal agents, such as paraben, chlorobutanol, phenol, sorbic acid, or the like. Prolonged absorption of injectable pharmaceutical forms may be caused by the use of agents that delay absorption, such as aluminum monostearate and gelatin.

Another embodiment of the present invention relates to an isolated polynucleotide consisting of a nucleic acid sequence of SEQ ID NO: 7 or SEQ ID NO: 10, and a vector including the polynucleotide or DNA encoding the same.

A polynucleotide of SEQ ID NO: 7 includes a CSDE1-binding motif nAAGmA in a wild-type sequence of a 5'UTR of a mouse Gpr151 gene (where n is c, g, or u, and m is a, u, or g), and the nAAGmA is a representative example of a polynucleotide that has been modified to be present as an intact single-strand and is referred to as 5'UTRm in the embodiment of the present invention for convenience' sake. According to one embodiment of the present invention, it was confirmed that 5'UTRm exhibits more stable binding to CSDE1 than a wild type sequence (5'UTR$_{WT}$) of 5'UTR of a Gpr151 gene (FIG. 4K), and induces significantly stronger nerve regeneration than 5'UTR$_{WT}$ expression (FIGS. 5A and 5B).

A polynucleotide of SEQ ID NO: 10 includes a CSDE1-binding motif nAAGmA in a wild-type sequence of a 5'UTR of a human Gpr151 gene (where n is c, g, or u, and m is a, u, or g), the nAAGmA is a representative example of a polynucleotide that has been modified to be present as an intact single-strand and is referred to as hGPR151_MUT in the embodiment of the present invention for convenience' sake. According to one embodiment of the present invention, it was confirmed that hGPR151_MUT induces stronger nerve regeneration than a wild type sequence (hGPR151_WT) (FIGS. 9A and 9B).

Since a polynucleotide and a vector have been described in detail above, redundant descriptions will be omitted.

A polynucleotide of the present invention may be obtained by appropriately using technologies known in the art. For example, the polynucleotide may be chemically synthesized using a known technology or produced by a recombinant method. For example, the polynucleotide may be chemically synthesized using appropriately protected ribonucleoside phosphoramidites and a conventional DNA/RNA synthesizer. As another example, the polynucleotide may be expressed from a recombinant circular or linear DNA plasmid using an appropriate promoter, and the plasmid may further include a polyT termination sequence, but is not limited thereto. As another example, the polynucleotide may be expressed from a recombinant viral vector in cells, and the viral vector may include an appropriate promoter and an expression regulatory sequence for polynucleotide expression.

Hereinafter, the present invention will be described in more detail through the following examples. However, these are only for illustrating the present invention, and the scope of the present invention is not limited by these examples.

Experimental Materials and Methods

1. Information on Experimental Model and Experimental Subject

Primary embryonic DRG neuron culture: DRG tissues from mice at embryonic day 13.5 were separated in 0.05% trypsin-EDTA (Thermo Fisher Scientific, 25300054) and plated on poly-D-lysine (Sigma, P0899)/laminin (Thermo Fisher Scientific, 23017015)-coated dishes in a neurobasal medium (Thermo Fisher Scientific, 21103049) supplemented with 2% B-27(Thermo Fisher Scientific, 17504044), 1% Gutamax (Thermo Fisher Scientific, 35050061), 1 μM 5-fluoro-2'-deoxyuridine (Sigma, F0503), 1 μM uridine (Sigma, U3003), 1% penicillin-streptomycin (Thermo Fisher Scientific, 15070063), and 50 ng/ml 2.5S nerve growth factor (Envigo, BT-5017). For replating assay, cultured neurons were replaced with Dulbecco's Modified Eagle Medium (DMEM, Hyclone, 500 ml sh30243.01)/0.05% trypsin-EDTA mixture (1:1) at DIV 5. Neurons were incubated in a 37° C., 5% $CO_2$ incubator for 5 min. Then, neurons were pipetted with the above-described culture medium. Cells were then dissociated by gentle pipetting and transferred to new Lab-Tek chamber slides coated with poly-D-lysine/laminin. After replating, neurons were incubated for 12 to 14 hours at 37° C. with 5% $CO_2$, and then fixed in 4% paraformaldehyde (Biosesang, P2031) for 15 min at room temperature. The axon length was measured and assessed using the Neurite Tracer for ImageJ. Animal models: (model organism: name used in the study: allele symbol). Mouse: RiboTag: p122$^{tm1.1Psam}$; mouse: Advillin-Cre: Avil$^{tm2(cre)Fawa}$; mouse: CD-1: Crl: CD1 (ICR); mouse: C57BL/6J: C57BL/6J; mouse: KO: Gpr151$^{tm1Dgen}$. For in vivo animal studies, all the experiments were carried out in accordance with the Korea University Institutional Animal Care & Use Committee (KU-IACUC). Mice were anesthetized using 3% isoflurane in oxygen until unresponsive to toe pinch to confirm that the mouse is unconscious and kept on a heating pad for the duration of the surgery. The surgery site was shaved and disinfected using organic iodine of a chlorhexidine solution. All surgery instruments were disinfected using autoclave and a bead sterilizer. Mice were fed a diet (PicoLab 5053, Purina) and maintained on a 12 hour-light/dark cycle (6 am to 6 pm). Male and female mice were housed in groups of up to 5 mice per cage. Age-and sex-matched male mice were used at the indicated age. The RiboTag mouse carries a ribosomal protein gene with a floxed C-terminal exon followed by an identical exon tagged with hemagglutinin (HA) epitope. When RiboTag is crossed to a mouse expressing a cell-type-specific Cre recombinase, expression of the epitope-tagged protein is activated in the cell type of interest. A homozygote RiboTag mice (Rp122HA) obtained from Jackson Laboratory and an Advillin-Cre driver line were crossed. Cre-positive RiboTag animals (Rp122HA+/+; advillin-Cre+/−) and the littermate control (Rp122HA+/+; advillin-Cre−/−) mice were generated by crossing Rp122HA+/+; advillin-Cre+/− male with Rpl22HA+/+ female. Three-months or older mice were used for sciatic nerve surgery. Mice sciatic nerve was unilaterally exposed through a small incision made to the skin and muscles at a mid-thigh level. Then, the sciatic nerve was dissected by forceps, and the incision was closed by nylon suture. Afterwards, the animals were subjected to post-operation care until euthanized for analysis.

2. Gene Delivery Using Virus

Lentivirus-mediated gene delivery was used to knock down a target mRNA or overexpress an exogenous gene in embryonic neurons. Lentivirus was prepared with Lenti-X packaging Single Shots (Takara, 631275) according to the manual. For in vitro gene delivery, the Lentivirus was applied to embryonic neuron culture at DIV2. For in vivo gene delivery, AAV (serotype 9) (10 µl) was injected to neonatal CD-1 mice by facial vein injection using a Hamilton syringe (Hamilton, 1710 syringe with 33G/0.75-inch small hub removable needle). 10 µl of AAV virus was tested, and the expression of GFP and the target gene in the sciatic nerves and DRG was confirmed through Immunohistochemistry and RT-qPCR analysis.

3. Antibody array

Embryonic DRG neurons were rinsed with 1× PBS and then collected by gentle centrifugation. Cell pellets were collected at DIV 6. Frozen pellets of eDRG cells were sent to ebiogen Inc. (Seoul, Korea) for antibody array and initial data analysis. The Signaling Explorer Antibody Microarray (SET100), consisting of 1,358 antibodies, was provided from Full Moon BioSystems, Inc. (Sunnyvale, CA, USA).

4. Ribosome-Binding RNA

The LA,5 DRG tissues were dissected at 24 hours after sciatic nerve lesion from both Cre-positive and Cre-negative RiboTag mice. The DRG tissues were homogenized in a lysis buffer (1% NP-40, 20 mM HEPES-KOH, 5 mM $MgCl_2$, 150 mM KCl, 1 mM DTT, SUPERase In (Thermo Fisher Scientific, AM2694) and Complete EDTA-free Protease Inhibitor Cocktail (Sigma, 11873580001)) in the presence of cycloheximide (Sigma, C7698-1G) and rapamycin (Sigma, R0395), and then post-mitochondrial fractions were collected. A previously reported a Translating Ribosome Affinity Purification (TRAP) protocol was followed (Shigeoka et al., 2016). Precleared ribosome-mRNA complexes were immunoprecipitated by anti-HA antibody and Dynabeads Protein G (Thermo Fisher Scientific, 10004D). Total RNA was extracted from the ribosome-mRNA complex using the RNeasy mini kit (Qiagen, 217084), and genomic DNA contaminants were eliminated through in-column DNase treatment. RNA samples were quantitatively and qualitatively analyzed using Nanodrop.

5. Immunoprecipitation of RNA-Binding Proteins

L4,5 DRG tissues were dissected at 24 hours after sciatic nerve lesion. Tissues were homogenized in a TRAP lysis buffer. CSDE1 was immunoprecipitated by an anti-CSDE1 antibody (Abcam, ab201688) pre-bound to Dynabeads Protein G (Thermo Fisher Scientific, 10004D) from total 82 µg input lysates for 16 hours at 4° C. The precipitants were washed five times using DynaMag-2 (Thermo Fisher Scientific, 12321D) and subjected to reverse transcription for quantitative real-time PCR.

6. Library Preparation and Nanopore Sequencing and Analysis

Nanopore PCR-cDNA sequencing kit (SQK-PCS109, Oxford Nanopore Technologies) was used according to the manufacturer's instructions to prepare a Nanopore library from the bound total RNA. The VN primer was annealed to the RNA to target poly A tail, and first-strand cDNA was synthesized by Maxima H Minus Reverse Transcriptase (Thermo Fisher Scientific, EP0752). Afterwards, the RNA-cDNA hybrid was purified using A gencourt AMPure XP magnetic beads (Beckman Coulter, A63880). PCR was performed using 2× LongAmp Taq Master Mix (New England Biolabs, M0287S) to select full-length transcripts followed by a second purification step using Agencourt beads (as described above). Purified cDNA was resuspended by adding 12 µl elution buffer and resuspending the beads and incubated for 10 minutes at room temperature, beads were pelleted again, and the supernatant (pre-sequencing mix) was transferred to a new tube. The Rapid Adapter was then linked to the cDNA library. Nanopore sequencing was performed using an R9.4 SpotON flow cell (FLO-MIN106, ONT) with a MinION sequencer according to the manufacturer's instructions. MinION sequencing was controlled using Oxford Nanopore Technologies MinKNOW software according to the manual. After basecalling, the Nanopore read data were aligned to the Mus musculus reference sequence (GRCm38.p6, GCA_000001635.8) and transcripts using MiniMap2. After mapping, all SAM files were parsed into BAM files classified using SAMtools v1.3.1. The RT adapter was annealed to the RNA for reverse transcription and reverse-transcribed RNA was then purified using Agencourt RNAClean XP magnetic beads (Beckman Coulter, A63880). The purified RNA was eluted from RNAClean beads (included in the kit) in 21 µl elution buffer. Then, a sequencing adapter was linked to the library.

7. PNS Axon Regeneration Analysis

For pre-conditioning injury, the right sciatic nerve of age-and sex-matched mice was crushed with forceps, and the L4,5 DRG was dissected from the spinal cord on the indicated days after injury. Adult DRG was dissociated for 15 minutes at 37° C. using Liberase™ (Roche, 5401119001), DNase I (Sigma, 11284932001), bovine serum albumin (Sigma, A2153), and trypsin-EDTA. The dissociated DRGs were gently crushed by pipetting, plated on culture dishes coated with poly-d-lysine (Sigma, P0899) and laminin (Thermo Fisher Scientific, 23017015) in DMEM with 10% fetal bovine serum (Thermo Fisher Scientific, 26140079), 1% penicillin-streptomycin, (Thermo Fisher Scientific, 15070063) and 1% Glutamax (Thermo Fisher Scientific, 35050061) and 50 ng/ml nerve growth factor (Envigo, BT-5017) and incubated in a humidified incubator at 37° C./5% $CO_2$. Sciatic nerves were dissected at 3 days after crush injury and dissected, sectioned, and immunostained with TUJ1 antibody and anti-SCG10 antibody. To visualize the regenerating axons in a single panel image, multiple images were taken along the nerve and automatically monitored in a microscope (EVOS FL Auto Cell Imaging System, Thermo Fisher Scientific, AMC1000). SCG10 fluorescence intensity was measured along the length of the nerve sections using ImageJ software. SCG10 intensity plots were drawn with average intensity calculated from 50 pixels. The regeneration index, calculated by measuring the average SCG10 intensity from the site of injury to the distal region, is defined as the position along the length of the nerve with maximum SCG10 intensity, and is associated with TUJ1 labeling, where nerve deformation and axonal destruction are confirmed.

8. CNS Axon Regeneration Analysis

To analyze in vivo CNS axon regeneration in an optic nerve injury model, 1.5 µl of AAV was injected with a pulled glass needle to vitreous of eye. The conjunctiva from the orbital part of the eye was cleared in order to expose the optic nerve, which was crushed for three seconds with Dumont #5 forceps (Fine Science Tools, 11254-20) and special care was taken not to damage the vein sinus. To avoid drying of the eye, a saline solution was applied before and after optic nerve crush. For cholera toxin b (CTB) axon tracing, 1% atropine sulfate solution (Bauch & Lomb) was applied to the eye to induce pupil dilation. A pulled glass needle was introduced intp the vitreous through the ora serrate and 2 µl of 2 µg/µl CTB (Thermo Fisher Scientific, C34777) was injected. For optic nerve fixation and sectioning, mice were sacrificed at two days after CTB injection and both the eyes and the optic nerves were fixed by immersion in 4% paraformaldehyde solution for two hours. After being washed three times in PBS, eyes were transferred to 30% sucrose solution for 24 hours at 4° C. The optic nerves were then dissected with micro scissors (Fine Science Tools, 15070-08), sectioned at 11 μm in a cryostat, and mounted in ProLong Gold (Thermo Fisher Scientific, P36931) mounting medium. The optic nerve sections were imaged with EVOS FL Auto Cell Imaging System. The numbers of regenerating axons at different distances from the injury site were estimated following the published protocol described by Park et al., 2008. The numbers of regenerating axons crossing lines set at 0.2, 0.5, 0.8 and 1 mm from the injury site were quantified in five different slices per optic nerve using ImageJ. The cross-sectional width of the optic nerve was used to estimate the number of regenerating axons per μm. The total number of regenerating axons per each optic nerve at certain distance from the injury site ($\Sigma a_d$) was estimated using the following formula:

$$\sum\nolimits_{a_d} = \pi \times (\text{optic nerve radius})^2 \times [\text{average axons}/\mu\text{m}]/11\,\mu\text{m}.$$

For statistical analysis, the average numbers of regenerating axons from control and 5'UTRm-expressing mice at each distance were compared using Student's test.

9. Fluorescent In Situ Hybridization (FISH)

Gpr151 mRNA was detected by a pair of target probe (RNAscope Probe-Mm-Gpr151, ACD, 317321) following the manufacturer's instructions. L4,5 DRG tissues were fixed in 4% paraformaldehyde and permeabilized. The fixed sample tissues were cryo-blocked with optimal cutting temperature (OCT) compound and sectioned in a 10 μm thickness with cryotome. The sections were each dehydrated with 50%, 70% to 100% ethanol for five minutes at room temperature and then air-dried for five minutes at room temperature. The tissue sections were incubated in Protease 4 (ACD, kit RNAscope, 322000) solution for 15 minutes at room temperature. For washing, phosphate-buffered saline was applied five times to the tissue sections. A target probe was pre-heated at 40° C., and then the probe was applied to the tissue sections which were incubated for two hours at 40° C. The slides were then washed twice with a wash buffer (ACD, kit RNAscope, 322000). The fluorescence probes Amp-1-FL, Amp-2-FL and Amp3-FL were applied to tissue sections for 30 min at 40° C. Finally, Amp-4-FL was applied, and the sections were incubated for 15 min at 40°° C. The prepared samples were mounted and analyzed under a confocal microscope (Zeiss, LSM700).

10. Biotin-RNA Pull-Down Assay and Mass Analysis

All the RNA baits used for a pull-down assay were synthesized by Integrated DNA Technologies Inc. (IDT). Total protein lysates were prepared from DRG tissues dissected from 6-week old CD-1 mice and lysed in a lysis buffer [1% NP-40, 20 mM HEPES-KOH, 5 mM $MgCl_2$, 150 mM KCl, 1 mM DTT, SUPERase In (Thermo Fisher Scientific, AM2694) and Complete EDTA-free Protease Inhibitor Cocktail (Sigma, 11873580001)]. 1 mg of protein lysate was applied as an input for each pull-down condition. The quantified protein input was incubated with the indicated biotin-RNA baits for 16 hours at 4° C., followed by incubation with Dynabeads MyOne Streptavidin T1 (Thermo Fisher Scientific, 65601) for additional one hour at 4° C. with rotation. Magnetic beads complexes were washed and recovered by a magnet (Thermo Fisher Scientific, 12321D) according to the manufacturer's instructions. Total protein from the precipitated magnetic beads were eluted by incubating at 95° C. for 10 min in a 1× SDS-PAGE sampling buffer, and then subjected to SDS-PAGE separation. To identify the eluted proteins by a mass spectrometry analysis, protein bands from the PAGE gel were visualized by a Coomassie staining method and sliced to perform in-gel digestion. All the mass spectrometry analysis including sample preparation were performed by Yonsei Proteome Research Center (YPRC, Seoul).

11. Information on Sequences used Experiments

TABLE 1

| RNA sequence (bait) | | |
|---|---|---|
| | Sequence | SEQ ID NO. |
| 5'UTR of Gpr151-human (hGpr151_WT) | CAAACCUAAAUAAGAAUCUAACUUCUGUAAG AAGCUGUGAAGAGUG | 1 |
| 5'UTR of Gpr151-rat | ACCAACCUAAUAAGAAGCUAACAUCUGCAGG GAGGAGCUGG | 2 |
| 5'UTR of Gpr151-mouse | CCAACCUAAACAAGAAGCUACCAUCUGCAGG GAGGAGCUUG | 3 |
| 5'UTR of Gpr151-ACSDE1 | CCAACCUAAAGCUACCAUCUGCAGGGAGGAG CUUG | 4 |
| 5'UTR of Gpr151-4X mutant | ACAAGAAGACAAGAAGACAAGAAGACAAGA AG | 5 |
| 5'UTR-h of Gpr151 (mouse) | CCAACCUAAAC | 6 |
| 5'UTRm of Gpr151 (mouse) | CCAACCUAAACAAGAAGCUACCAUCUGCAGG GAGGUCGAAG | 7 |
| 5'UTRΔ of Gpr151 (mouse) | CCAACCUAAACAAGAAGC | 8 |
| 5'UTRmΔCSDE1 of Gpr15 (mouse) | CCAACCUAAAGCUACCAUCUGCAGGGAGGUC GAAG | 9 |
| hGpr151_MUT (human) | CAAACCUAAA UAAGAAUCUA ACUUCUGUAA GAAGGACUGA AGAGUG | 10 |

TABLE 2 shRNA sequence

| | Sequence | SEQ ID NO. |
|---|---|---|
| Gpr151-targeted shRNA | GCAAAGATTTCTGCTTTCAAA | 11 |
| Csde1-targeted shRNA | TGCTGTAAGTGCTCGTAATAT | 12 |
| Khdrbs1-targeted shRNA | GCATGTCTTCATTGAAGTCTT | 13 |

TABLE 3 qPCR primer sequence

| | Sequence | SEQ ID NO. |
|---|---|---|
| Gpr151 Forward | CTGGGTTTGCCGACACCAAT | 14 |
| Gpr151 Reverse | AGAGAGACGGAATGATGGTCC | 15 |
| Jun Forward | CCTTCTACGACGATGCCCTC | 16 |
| Jun Reverse | GGTTCAAGGTCATGCTCTGTTT | 17 |
| Atf3 Forward | GAGGATTTTGCTAACCTGACACC | 18 |
| Atf3 Reverse | TTGACGGTAACTGACTCCAGC | 19 |

Experimental results

Figure 1C:
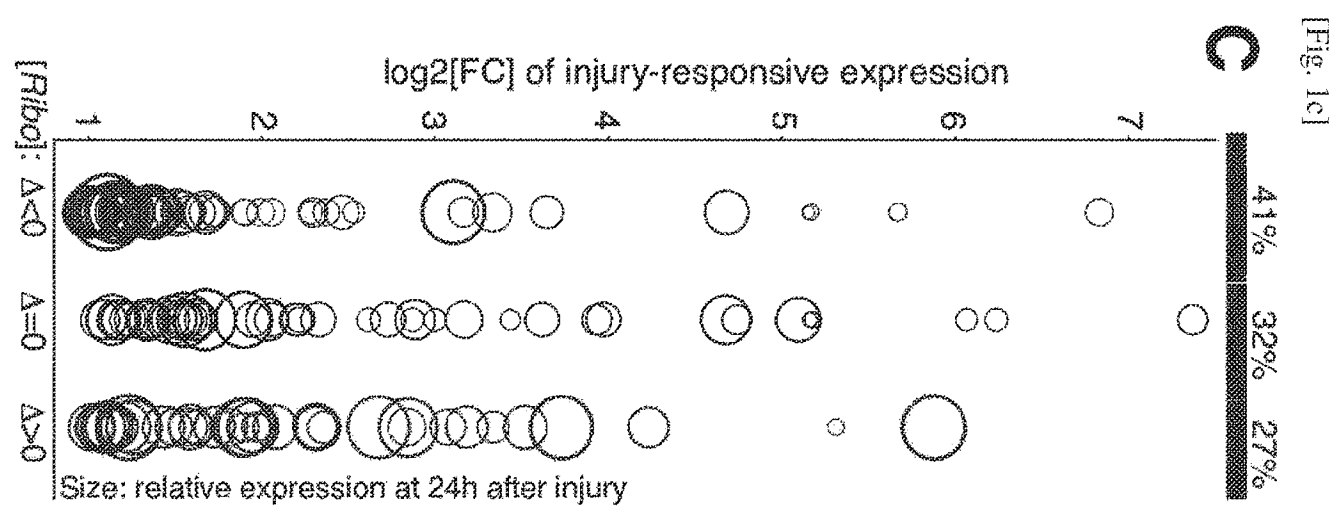

Example 1. Injury-Responsive Protein-Coding mRNA Exhibits Differential Ribosome-Binding Efficiency For analysis based on ribosome-binding efficiency of mRNA in DRG, Ribo Tag mice were crossed with Advillin-Cre mice to produce Adv-Rpl22HA mice, which specifically express HA-tagged ribosomal protein L22 from sensory neurons of DRG tissues. (FIG. 1A). This mouse model allows separation of translating RNA through anti-HA immunoprecipitation. To introduce axonal injury, the sciatic nerve of the Adv-Rpl22HA mice was crushed, and the L4-5 DRG tissue was dissected at 24 hours after injury. Total RNA and ribosome-binding RNA were analyzed by RNA sequencing to determine transcript and ribosome-binding efficiency, respectively (FIG. 1B). To assess the relationship between the two profiles, injury-induced transcripts were categorized into three groups based on their injury responsiveness in ribosome-binding data: mRNAs showing enhanced ribosome-binding, mRNAs showing unchanged ribosome-binding, and mRNAs showing reduced ribosome-binding. It was confirmed that a limited number of injury-induced mRNAs were recruited to ribosomes after injury (FIG. 1C). Of the 149 protein-coding genes upregulated two folds or more after injury, only 40 genes (27%) showed stronger binding to ribosomes after injury, and although many genes in this group were significantly upregulated after axonal injury, 48 genes (27%) did not show a significant difference in their ribosome-binding efficiency (FIG. 1C). Twenty-five genes (41%) showed reduced ribosome-binding after injury. These results show that transcription and ribosome-binding often appear unrelated to injury-induced protein-coding DEGs.

Example 2. Gpr151 is Highly Upregulated in DRG Neurons After Injury, Only at mRNA Level and Not at Protein Level To study the role of injury-induced mRNAs in regeneration, single-exon genes were first taken into consideration, because they make allow for tracking a single type of mRNA transcript without RNA splicing. Three candidate genes, Gpr151, Sox11, and Jun, which consist of a single exon and are significantly upregulated after injury, were identified (FIG. 1D). While ribosome-binding of Jun and Sox 11 mRNAs was induced after injury, the level of ribosome-bound Gpr151 was not changed by nerve injury. Gpr151, the most strongly upregulated of the three genes, has been identified as a injury-responsive gene in previous axon injury-related transcriptome studies, but the role of this protein in axon regeneration remains unclear. On the other hand, Jun has been established as an indicator of nerve injury at both mRNA and protein levels. Therefore, it was decided to compare Gpr151 and Jun to monitor their protein and mRNA levels after injury. After sciatic nerve axotomy, the mouse DRG tissue was dissected and analyzed by qPCR and Western blot analysis. Significant upregulation of Jun was observed at both the mRNA and protein levels through qPCR and Western blot analysis, respectively, which is consistent with previous reports (FIGS. 1E and 1F). However, despite an approximately 30-fold increase in the Gpr151mRNA level, the protein level was not upregulated, which is consistent with the results from RNA-sequencing data. This was confirmed through fluorescence in situ hybridization (FISH) and immunohistochemistry (IHC) analyses of DRG sections (FIGS. 1G and 1H). These results indicate that the transcriptional control of Gpr151 is clearly unrelated to the strong upregulation of the mRNA and that Gpr151 is a suitable model in testing the hypothesis that injury-induced mRNA performs a ribosome-independent, non-coding RNA function in regenerating neurons.

Example 3. Gpr151 is Required for Axon Regeneration and Functions Through its 5'UTR To investigate the role of Gpr151 in axon regeneration, the need for its mRNA expression was first tested using shRNA targeting Gpr151 in cultured embryonic DRG neurons. Axonal regrowth was assessed by measuring neurite length from replated neurons following lentiviral transduction of shRNA. It was found that knockdown of Gpr151 significantly reduced neurite regrowth (FIGS. 2A and 2D). Next, to test whether the role of Gpr151 mRNA is dependent on its protein translation, two types of Gpr151 constructs were designed: (1) CDSw, in which the 5'UTR is followed by a protein-coding region (CDS) of Gpr151; and (2) CDSm, which is identical to CDSw except that the start codon is mutated from AUG to AUC (FIG. 2B). A Western blot analysis showed that the CDSm construct was inefficient in producing Gpr151 protein in DRG neurons (FIG. 2C). These constructs were overexpressed in DRG neurons in combination with shRNA to monitor their ability to restore regeneration potential. First, an in vitro replating assay showed that CDSw overexpression did not fully restore the regeneration capacity when endogenous Gpr151 was knocked down. On the other hand, CDSm successfully restored axon regeneration capacity (FIGS. 2A and 2E). Based on these results, it was hypothesized that Gpr151 mRNA and its protein regulate axon regeneration in different ways.

To test this hypothesis, the 5'UTR and CDS regions of Gpr151 were each expressed to monitor their abilities to alter regeneration capacity (FIG. 2F). Overexpression of Gpr151 protein through CDS did not enhance axonal regeneration and actually inhibited it (FIGS. 2F and 2G). However, overexpression of only the 5'UTR of Gpr151 promoted axonal regeneration capacity, indicating that the 5'UTR is sufficient to promote regeneration and that the 5'UTR is important in a non-coding function of Gpr151 required for regeneration in replated neurons (FIGS. 2A, 2D, 2F and 2G). These results suggest that Gpr151 is required to promote axonal regeneration through the function of the 5'UTR thereof, whereas overproduction of Gpr151 protein may inhibit axonal regrowth in injured DRG neurons.

To validate the different roles of Gpr151 mRNA and protein in vivo, Gpr151-targeted mutant mice (KO), in which the Gpr151 CDS is disrupted by the LacZ cassette and thus Gpr 151 protein production is impaired, were used. In particular, the KO mice expressed the mutant mRNA (Gpr151-UTR-LacZ) along with the normal 5'UTR (FIG. 3A). First, injury-responsive upregulation of normal and mutant Gpr151 transcripts was tested in the DRG tissues from each of the control and KO mice 1 and 3 days after the introduction of axonal injury. It was found that the level of Gpr151-UTR-LacZ RNA expressed in the KO mice was threefold higher than that of the normal Gpr151 mRNA expressed in the controls at 1 day after injury. Expression of Gpr151-UTR-LacZ RNA continued for 3 days after injury (FIG. 3B).

Afterwards, the axon regeneration capacity was monitored using an in vivo axon regeneration assay in which regenerating axons were specifically labeled with an anti-SCG10 antibody. The KO mice showed enhanced axonal regeneration after the sciatic nerve injury compared to the control mice (FIGS. 3C, 3D, and 3E). To confirm whether this enhancement was due to a neuronal effect, the regeneration capacity of the cultured DRG neurons from the control and the KO mice was monitored under a preconditioned injury paradigm. In the absence of the preconditioned injury, the cultured DRG neurons from both the control and the KO mice failed to project their axons strongly (FIG. 3F). However, the preconditioned injury (+injury) strongly promoted the regeneration capacity, and the DRG neurons from the KO mice exhibited longer axons compared to the control mice (FIGS. 3F, 3G, and 3H). In the KO mice, the number of DRG neurons with axons less than 100 μm long was less than 50% of the control mice, whereas the KO mice had twice as many neurons with axons longer than 300 μm compared to the controls (FIG. 3I).

Collectively, the Gpr151 protein-null mice showed no obstacles to axonal regeneration, indicating that the Gpr151 protein is not required for efficient axonal regrowth after injury. Instead, the protein-null mice projected their axons more strongly, which supports a negative function of the Gpr151 protein in axon regeneration. It is also possible that the KO mice exhibit stronger regeneration capacity due to more immediate upregulation of Gpr151-UTR-LacZ compared to the normal Gpr151 mRNA from the control mice at 1 day after injury (FIG. 3B). Collectively, these data show that the 5'UTR of Gpr151 (Gpr151-5'UTR) plays a regulatory role in promoting axonal regeneration by altering neurophysiology.

Example 4. 5'UTR of Gpr151 Binds to CSDE1, Which is a Potential Negative Regulator of Axon Regeneration To understand the molecular mechanism underlying the role of Gpr151-5'UTR, an RNA pull-down analysis and mass spectrometry were performed to identify proteins that bind to the 5'UTR of Gpr151 mRNA. A total of 25 proteins were identified through high confidence score and mass match (FIG. 4A). From the identified RBP proteins, attention was paid to cold shock domain-containing protein E1 (CSDE1) due to the consensus CSDE1-binding sequence nAAGnA positioned at −32 bp from the start codon in the 5'UTR of Gpr151. It was found that when the rat and human genes were aligned, the CSDE1-binding motif has been evolutionarily conserved because both 5'UTRs have binding sequences at −β32 bp (rat) or −37 bp (human) from the start codon FIG. 4B). This suggests that Gpr151 mRNA interacts with CSDE1 through its 5'UTR, potentially playing an evolutionarily conserved role in mammals.

Figures 4G, 4H:
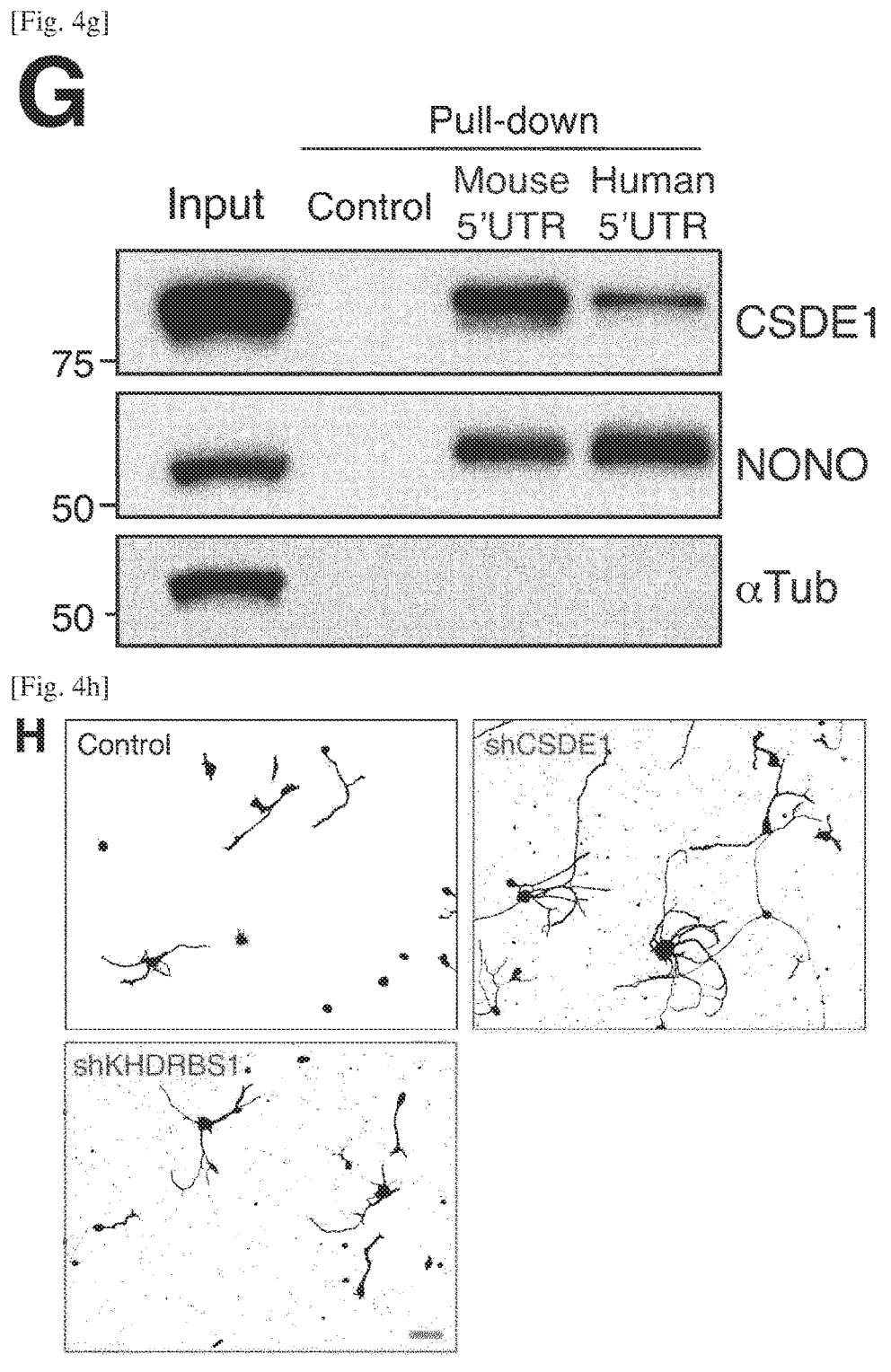

The interaction between 5'UTR and CSDE1 was confirmed by an RNA pull-down analysis using biotinylated 5'UTR as a bait and a Western blot analysis using an anti-CSDE1 antibody (FIG. 4C). In addition, this interaction was reversely validated using immunoprecipitation of CSDE1 from DRG tissue lysates. CSDE1 was immunoprecipitated, and as a result of RT-qPCR for Gpr151, it was confirmed that Gpr151 mRNA upregulated by nerve injury was strongly related to CSDE1 (FIG. 4D). The rapid increase in CSDE1-bound Gpr151 mRNA shows clear contrast to its affinity for ribosomal complexes, which remained unchanged after injury (FIG. 1). To determine whether the CAAGAA sequence within the 5'UTR is important to the interaction with CSDE1, an RNA pull-down analysis was performed with a CAAGAA-deleted mutant (ΔCSDE1) and an artificial 32-mer RNA (4×) having only 4× repeated sequences of the A-CAAGAA-G sequence (FIG. 4E). Subsequent Western blot analysis showed that artificial RNA 4× had stable binding to CSDE1, while the interaction of ΔCSDE1 was considerably destabilized (FIG. 4F). It was confirmed that Human GPR151 mRNA also has a CSDE1-binding motif within its 5'UTR, and there is an interaction between CSDE1 and the 5'UTR of GPR151 (FIG. 4G). These results indicate that the CAAGAA sequence in the 5'UTR is mainly responsible for binding to CSDE1.

```
5'UTR_{WT}:
                                    (SEQ ID NO: 3)
CCAACCUAAACAAGAAGCUACCAUCUGCAGGGAGGAGCUUG

ΔCSDE1:
                                    (SEQ ID NO: 4)
CCAACCUAAA------GCUACCAUCUGCAGGGAGGAGCUUG

4X:
                                    (SEQ ID NO: 5)
ACAAGAAGACAAGAAGACAAGAAGACAAGAAG
```

Previous studies have reported that CSDE1 is a negative regulator of neural differentiation in human embryonic stem cells, and loss of CSDE1 promotes neural differentiation and neural tissue development, while overexpression of CSDEI hinders differentiation. Recently, more evidence for CSDE1-mediated axon development has been reported, which demonstrates that CSDE1 knockdown promotes neurite and axon growth. To investigate the role of CSDE1 in an axonal injury model, an in vitro axonal regeneration assay was performed using embryonic DRG neurons. As a result, it was found that knocking down CSDE1 promoted the regeneration capacity of neurons by up to about 50% (FIGS. 4H and 4I). KHDRBS1, an RPB also identified as a binding protein of Gpr151-5'UTR, was also knocked down to test its relationship with axon regeneration, but it did not affect axon regeneration, supporting the specific function of CSDE1. This presents the potential ability of CSDE1 as a negative regulator of axon regeneration and suggests that the function of CSDE1 in regeneration is regulated through interaction with the 5'UTR of Gpr151.

CSDE1 is known to regulate mRNA translation by binding to single-stranded RNA. Prediction of the RNA secondary structure of the 5'UTR showed that the 5'UTR of Gpr151 is partially single-stranded (FIG. 4J, colored letters in 5'UTR$_{WT}$). To explore the feasibility of manipulating the 5'UTR-CSDE1 interaction and the feasibility of manipulating the 5'UTR for possible applications, three 5'UTR mutant forms were produced: 1) h: the shortest 11-mer RNA without the CSDE1-binding motif; 2) 5'UTRm: the entire 5'UTR sequence, in which AGCUU at -5 bp is replaced with the complementary sequence UCGAA so that the binding motif CAAGAA becomes fully single-stranded; and 3) Δ: 5'-portion of the 5'UTR including the CDSE1-binding motif but lacking a stem-loop region (FIG. 4J).

```
5'UTR_WT:
                                    (SEQ ID NO: 3)
CCAACCUAAACAAGAAGCUACCAUCUGCAGGGAGGAGCUUG h:
                                    (SEQ ID NO: 6)
CCAACCUAAAC

5'UTRm:
                                    (SEQ ID NO: 7)
CCAACCUAAACAAGAAGCUACCAUCUGCAGGGAGGUCGAAG

Δ:
                                    (SEQ ID NO: 8)
CCAACCUAAACAAGAAGC
```

It was found that h does not bind to CSDE1, which reconfirms previous results obtained using ΔCSDE1 (FIG. 4F). However, both 5'UTRm and Δ exhibited more stable binding than 5'UTR$_{WT}$ (FIG. 4K), suggesting that the CAAGAA sequence in the 5'UTR is required for binding to CSDE1 and that when CAAGAA is single-stranded, this interaction is stabilized. Afterwards, Δ was used as a molecular competitor in a bait-competition pull-down assay (FIGS. 4L and 4M). As a result of the competition assay, it was found that an increase of the concentration of the competitor impaired the interaction between the 5'UTR and CSDE1 in both mouse Gpr151 and human Gpr151 (FIGS. 4L and 4M). Collectively, the results of the biochemical analysis demonstrate that CSDE1 is a biological interactor for Gpr151 mRNA and that the 5'UTR of Gpr151 mRNA is responsible for this interaction.

Example 5. 5'UTR of Engineered Gpr151 Promotes Axon Regeneration by Regulating CSDE1-Bound RNA Pool.

Because of the function of CSDE1 as a negative regulator of axon regeneration in vitro (FIGS. 4H and 4I), it was tested whether this function is regulated by its interaction with Gpr151-5'UTR. First, the regeneration capacity of 5'UTR$_{WT}$ was compared with that of 5'UTRm-overexpressing neurons to investigate whether the enhanced CSDE1-binding affinity of 5'UTRm affects its ability to promote axonal regeneration. It was found that 5'UTR$_{WT}$ promoted axon regeneration by up to 50% compared to the controls (FIGS. 5A and 5B), which is consistent with the results of the initial analysis (FIG. 2G). However, 5'UTRm expression induced significantly more robust regeneration than 5'UTR$_{WT}$ expression (FIGS. 5A and 5B). To validate that the enhanced function of 5'UTRm is required for binding to CSDE1, an additional mutation deleting the CSDE1-binding motif was introduced into 5'UTRm (5'UTRmΔCSDE1), and its effect on regeneration was tested. It was found that the 5'UTRmΔCSDE1 mutant did not promote axon regeneration as much as 5'UTR$_{WT}$ (FIG. 7), suggesting that the function of 5'UTR in regeneration is dependent on its physical binding to CSDE1.

```
5'UTRmΔCSDE1:
                                    (SEQ ID NO: 9)
CCAACCUAAA------GCUACCAUCUGCAGGGAGGUCGAAG
```

Since 5'UTRm effectively enhanced axon regeneration, the mechanism of CSDE1 regulation by 5'UTR was studied using a 5'UTRm mutant. Based on the known role of CSDE1 as an RBP that regulates interacting mRNAs, it was hypothesized that 5'UTRm can bind to CSDE1 to induce dissociation of interacting mRNAs and inhibiting the function of CSDE1. A comparative analysis was performed on 5'UTR-induced changes in CSDE1-binding mRNA, similar to the initial analysis for Rpl22-HA IP-seq shown in FIG. 1B, and 5'UTRm-dependent DEGs was assessed to control the mRNA level. In particular, the mRNA group (19.0% of the total) showed significant changes in its binding behavior to CSDEI after 5'UTRm overexpression, without corresponding changes in their expression levels (78.6%, $-1<$Log2 [fold change]$<1$). Many of these mRNAs (16.9% of the total) were dissociated from CSDE1, whereas a smaller group (2.7%) formed more stable bonds (FIG. 5C). Meanwhile, most of the mRNAs, including those that were differentially expressed (8.4%), did not show drastic changes in their interaction with CSDE1(80.4%). In addition, there were DEGs with mRNAs that were either upregulated (11.6%) or downregulated (9.9%) across twofold (FIG. 5C). As a result of the comparative analysis, it was found that 5'UTRm overexpression modulates the pool of CSDE1-bound coding mRNAs, suggesting that dissociation of these mRNAs is responsible for the CSDE1-dependent function of Gpr151-5'UTR. These results suggest that when an mRNA has a non-coding function through interaction with a specific RBP, regulation of the RBP function and interaction with its target mRNA may be an important molecular mechanism.

Since the biological consequence of 5'UTRm is enhanced regeneration capacity under axonal injury paradigm, the biological function of mRNA released from CSDE1 after 5'UTRm overexpression was investigated. The Database for Annotation, Visualization and Integrated Discovery (DAVID) tool was used for gene ontology and signaling pathway analysis. It was found that the known functions of the identified genes are particularly related to the regulation of protein localization and transport, and they also have abundant cytoskeletal remodeling, apoptosis, cell growth, and behavior control functions (FIG. 5D). In addition, the results of the pathway analysis showed that genes related to ribosomes and ribosome synthesis constitute a significant portion of the group of genes that were observed to be released from CSDE1 after 5'UTRm overexpression (FIG. 5). Genes related to neurodegenerative disorders such as Alzheimer's disease, Huntington's disease, Parkinson's disease, amyotrophic lateral sclerosis, and genes related to neurotrophin signaling or axon guidance were also abundant among the genes dissociated from CSDE1 (FIG. 5). This analysis shows that the unconventional experimental design in which the CSDE1-interactome was investigated showed a biological pathway that had not been identified in previous DEG studies related to peripheral nerve injury. In addition, genes identified in this pathway showed no significant changes in their expression levels, suggesting that simple DEG analysis may not capture them.

Finally, proteomic changes in the control and 5'UTRm-overexpressing neurons were analyzed. The results of an antibody-array analysis showed that 5'UTRm induced differential upregulation (14.9%) or downregulation (17.4%) of a total of 1,358 target proteins (FIG. 5F). These results were compared with CSDE1 IP-seq data, and it was found that an mRNA encoding a target protein showed distinct changes under CSDE1-binding conditions after 5'UTRm overexpression (FIG. 5G). A group of mRNAs including Eef1g, Fgfr2 and Song (red closed circles, 0.8%) were dissociated from CSDE1 when the 5'UTRm was overexpressed (FIG. 5G). However, a large number of mRNAs, including Ywhaz (open circles), showed no significant changes in their protein levels, and other groups released from CSDE1 (e.g., Tshz2, Tubb3, Mtal, and Nr2f2I) showed decreased protein levels. This suggests that when neuronal regeneration is promoted, the mRNAs released from CSDE1 have a different fate in terms of pathways to ribosomes or other RBPs.

Example 6. Expression of Engineered 5'UTR of Gpr151 Promotes Axon Regeneration In Vivo.

Figures 6A, 6B:
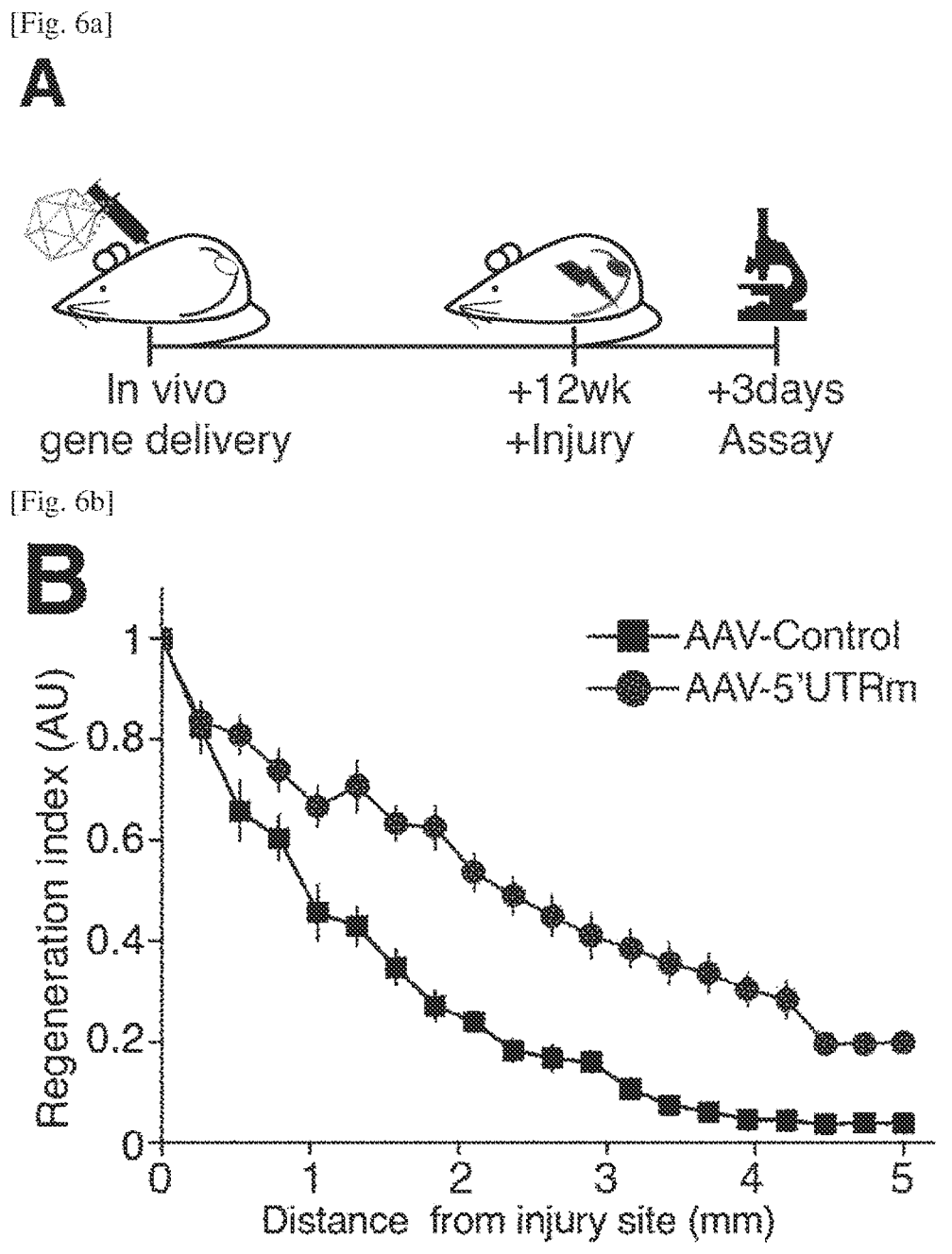

To test whether an engineered 5'UTR of Gpr151 is a potential tool to promote in vivo regeneration capacity, an AAV expressing the 5'UTRm was used for in vivo gene transfer in two different axon regeneration models. In a PNS axon regeneration assay, mouse sciatic nerves were injured through crush injury and dissected 3 days after injury (FIG. 6A). As observed in regeneration assays using cultured neurons, the sciatic nerves from the 5'UTRm-expressing mice showed a drastic increase in axonal regeneration (FIGS. 6B, 6C, and 6D). Similar results were reproduced in an analysis of CNS axon regeneration using an optic nerve injury model (FIG. 6F). The regenerated axons of the optic nerve were traced using CTB. It was found that 5'UTRm overexpression drastically increased the number of regenerating axons in the injured optic nerve (FIGS. 6F and 6G).

Neuronal injury responses in the PNS and CNS are known to be differentially regulated, resulting in significantly inefficient axonal regeneration in the CNS compared to the PNS (Curcio and Bradke, 2018; He and Jin, 2016; Mahar and Cavalli, 2018b). Therefore, to test whether the significant upregulation of Gpr151 is a molecular response specific to strongly regenerated PNS, qPCR was performed for Gpr151 in both systems. The Gpr151 mRNA was upregulated in the DRG neurons after sciatic nerve injury, whereas it was not observed in the retinal tissue after optic nerve injury (FIG. 6H). This suggests that the PNS and CNS may have different injury-responsive epigenetic mechanisms that regulate Gpr151 expression (Jiang et al., 2018). However, both systems showed similar results in promoting axon regeneration when Gpr151-5'UTRm was overexpressed. Therefore, components of downstream signaling regulated by the 5'UTR may function in both systems.

Example 7. Expression of 5'UTR of Human Gpr151 and its Variants Also Promotes Axon Regeneration The secondary structure of the 5'UTR wild type of human Gpr151(hGPR151_WT, SEQ ID NO: 1) is similar to that of the mouse, in which the CSDE1-binding motif in the 5'UTR of Gpr151 is partially single-stranded (FIG. 8, left). Accordingly, to expose the CSDE1-binding motif as a single-stranded structure, a variant (hGPR151_MUT, SEQ ID NO. 10) having a completely single-stranded binding motif UAAGAA was prepared by substituting the complementary sequence (FIG. 8, right). Similar to the experiment to investigate the effect of the 5'UTR of mouse Gpr151 on promoting axon regeneration, an in vitro regeneration assay was performed to investigate the effect of the 5'UTR of human Gpr151 wild type (hGPR151_WT) and its variant (hGPR151_MUT) on promoting axon regeneration. Embryonic DRG neurons were cultured and infected with the control (pLKO.1 null vector), hGPR151_WT (pLKO.1-hGPR151_WT), and hGPR151_MUT (pLKO.1-hGPR151_MUT) using lentiviruses. The axons were dissected on Day 5 under a microscope with a dissecting knife and fixed with formaldehyde after 30 hours, and then immunofluorescence staining was performed with SCG10 or b3-tubulin to label the axons. The results are shown in FIG. 9A, and FIG. 9B shows the results of a statistical analysis of the regeneration index calculated therefrom. In the control group, the degree of regeneration over 30 hours beyond the cutting line (red dotted arrow) was 23.7+6.6%, whereas in the case of hGPR151_WT overexpression, it increased by 202.6% to 48.0+10.2%, and in the case of hGPR151_MUT overexpression, the regeneration index was 56.3%, which was an increase of 237%. This confirmed that there was a significant difference based on an ANOVA analysis, and in particular, it was confirmed that MUT enhances the regeneration amplification ability more than WT. These results showed that, as in the case of the 5'UTR of mouse Gpr151, the wild type (Gpr151_WT) amplifies the regeneration ability also in humans, and the effect is further enhanced in the case of the modified variant (Gpr151_MUT).

From the above description, those skilled in the art will understand that the present invention can be implemented in other specific forms without changing its technical idea or essential features. Therefore, the embodiments described above should be understood in all respects as illustrative and not restrictive. The scope of the present invention should be construed as including the meaning and scope of the patent claims described below rather than the detailed description above, and all changes or modified forms derived from the equivalent concept thereof are included in the scope of the present invention.

---

What is claimed is:

1. An isolated polynucleotide consisting of a nucleic acid sequence of SEQ ID NO: 7 or SEQ ID NO: 10.

2. A vector comprising the polynucleotide of claim 1 or DNA encoding the same.

3. A method for treating a neurological disease caused by nerve injury comprising the step of:

administering to a subject a pharmaceutical composition comprising an isolated 5'-untranslated region (5'UTR) polynucleotide of a Gpr151 gene, a variant thereof, or a DNA encoding the 5'UTR polynucleotide or the variant, wherein the 5'UTR polynucleotide and the variant include nAAGmA in a wild-type sequence of the 5'UTR of a Gpr151 gene, wherein n is c, g or u, and m is a, u or g.

4. The method of claim 3, wherein the polynucleotide is derived from a mammal.

5. The method of claim 3, wherein the polynucleotide comprises a nucleic acid sequence of SEQ ID NO: 1, SEQ ID NO: 2 or SEQ ID NO: 3.

6. The method of claim 3, the variant further satisfies one or more of the following (a) to (d):

(a) having 85% or higher sequence identity with a wild-type sequence of 5'UTR of a Gpr151 gene and exhibiting nerve regeneration activity;

(b) the nAAGmA being single-stranded and the variant exhibiting nerve regeneration activity;

(c) including no stem-loop region and exhibiting nerve regeneration activity; and (d) all or a part of a 5' direction and/or 3' direction sequence of the nAAGmA being deleted and the variant exhibiting nerve regeneration activity.

7. The method of claim 3, wherein the variant comprises a nucleic acid sequence of SEQ ID NO: 7, SEQ ID NO: 8, or SEQ ID NO: 10.

8. The method of claim 3, wherein the polynucleotide, variant, or DNA is included in a vector.

9. The method of claim 8, wherein the vector is an adeno-associated viral vector (AAV), an adenoviral vector, a retroviral vector, a lentiviral vector, a herpes simplex virus vector, or an alphavirus vector.

10. The method of claim 3, wherein the neurological disease caused by nerve injury is a central nervous system (CNS) disease or a peripheral nervous system (PNS) disease.

11. The method of claim 10, wherein the neurological disease caused by nerve injury is Alzheimer's disease, dementia, multi-infarct dementia, frontotemporal dementia, dementia with Lewy bodies, mild cognitive impairment, corticobasal degeneration, Parkinson's disease, depression, metabolic brain disease, multiple systemic atrophy Multiple system atrophy, Huntington's disease, Pick's disease, progressive supranuclear palsy, epilepsy, dentatorubropallidol-uysian atrophy, spinocerebellar ataxia, glaucoma, stroke, brain ischemia, demyelinating disease, post-encephalitic parkinsonism, Tourette's syndrome, restless legs syndrome legs syndrome), attention deficit disorders with hyperactivity, spinal muscular atrophy, spinal bulbar muscular atrophy, amyotrophic lateral sclerosis (ALS), multiple sclerosis, primary lateral sclerosis, progressive bulbar palsy, paralysis, spinal cord injury, optic nerve injury, traumatic brain injury, diffuse axonal injury, or peripheral nerve trauma.

\* \* \* \* \*